(12) United States Patent
Yamaguchi et al.

(10) Patent No.: US 8,556,237 B2
(45) Date of Patent: Oct. 15, 2013

(54) REDUCED WATER MIST GENERATING DEVICE AND ELECTRIC APPARATUS

(75) Inventors: Tomohiro Yamaguchi, Moriyama (JP); Junpei Ohe, Hirakata (JP); Yukiko Mishima, Takatsuki (JP); Hiroshi Suda, Takatsuki (JP); Yukiyasu Asano, Kobe (JP); Yasuhiro Komura, Shijonawate (JP); Yoshinori Sainomoto, Sanda (JP)

(73) Assignee: Panasonic Corporation, Osaka (JP)

( * ) Notice: Subject to any disclaimer, the term of this patent is extended or adjusted under 35 U.S.C. 154(b) by 393 days.

(21) Appl. No.: 13/061,845

(22) PCT Filed: Sep. 18, 2009

(86) PCT No.: PCT/JP2009/066365
§ 371 (c)(1),
(2), (4) Date: Mar. 2, 2011

(87) PCT Pub. No.: WO2010/035707
PCT Pub. Date: Apr. 1, 2010

(65) Prior Publication Data
US 2011/0162528 A1    Jul. 7, 2011

(30) Foreign Application Priority Data

| Sep. 25, 2008 | (JP) | 2008-246951 |
| Sep. 25, 2008 | (JP) | 2008-246952 |
| Sep. 30, 2008 | (JP) | 2008-254966 |
| Sep. 30, 2008 | (JP) | 2008-254967 |
| Sep. 30, 2008 | (JP) | 2008-254968 |
| Sep. 30, 2008 | (JP) | 2008-254970 |

(51) Int. Cl.
*B01F 3/04* (2006.01)

(52) U.S. Cl.
USPC .................. 261/78.2; 261/142

(58) Field of Classification Search
USPC .................. 261/78.2, 142
See application file for complete search history.

(56) References Cited

U.S. PATENT DOCUMENTS

| 4,135,370 A | 1/1979 | Hosoda et al. |
| 5,478,449 A | 12/1995 | Hayakawa |
| 7,350,317 B2 | 4/2008 | Matsui et al. |

(Continued)

FOREIGN PATENT DOCUMENTS

| CN | 1762840 | 4/2006 |
| JP | 04193235 A * | 7/1992 |

(Continued)

OTHER PUBLICATIONS

U.S. Appl. No. 13/120,006 to Yukiko Mishima et al., filed Mar. 21, 2011.

(Continued)

*Primary Examiner* — Robert A Hopkins
(74) *Attorney, Agent, or Firm* — Greenblum & Bernstein, P.L.C.

(57) ABSTRACT

A reduced water mist generating device (1) is provided with a water acquiring section (3) that acquires water for generating reduced water, a reduced water generating unit (U) that generates the reduced water from the acquired water, a reduced water atomizing section (6) that atomizes the generated reduced water, and a spraying section (7) that sprays the atomized water. With such a configuration, the reduced water can be generated from water, drifted in the form of a mist in a space, and caused to arrive at an object.

30 Claims, 26 Drawing Sheets

(56) References Cited

U.S. PATENT DOCUMENTS

| | | |
|---|---|---|
| 2004/0020070 A1 | 2/2004 | Ito |
| 2010/0025505 A1 | 2/2010 | Suda et al. |
| 2010/0044475 A1 | 2/2010 | Nakada et al. |
| 2010/0133367 A1 | 6/2010 | Yano et al. |

FOREIGN PATENT DOCUMENTS

| | | |
|---|---|---|
| JP | 7-232114 | 9/1995 |
| JP | 2749258 | 5/1998 |
| JP | 10339484 | 12/1998 |
| JP | 11-195947 | 7/1999 |
| JP | 2001-79549 | 3/2001 |
| JP | 2002191426 | 7/2002 |
| JP | 2003088867 | 3/2003 |
| JP | 2003259733 | 9/2003 |
| JP | 3464279 | 11/2003 |
| JP | 2004192944 | 7/2004 |
| JP | 2004268003 | 9/2004 |
| JP | 2005105289 | 4/2005 |
| JP | 2005164139 | 6/2005 |
| JP | 2005201583 | 7/2005 |
| JP | 2005254208 | 9/2005 |
| JP | 2006095502 | 4/2006 |
| JP | 2006-334385 | 12/2006 |
| JP | 2007-117970 | 5/2007 |
| JP | 2007125461 | 5/2007 |
| JP | 2007155204 | 6/2007 |
| JP | 2007-190084 | 8/2007 |
| JP | 2007254435 | 10/2007 |
| JP | 2008126139 | 6/2008 |
| JP | 2008131872 | 6/2008 |

OTHER PUBLICATIONS

Japan Office action, mail date is Nov. 20, 2012.
Search report from E.P.O., mail date is Jan. 21, 2013.
China Office action, mail date is May 21, 2013.

* cited by examiner

FIG. 15A
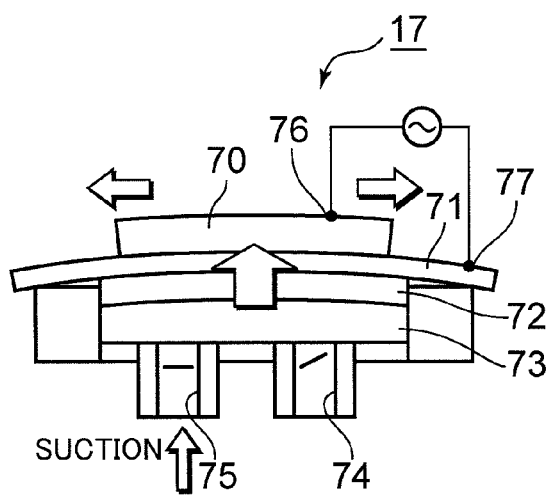
SUCTION
FIG. 15B
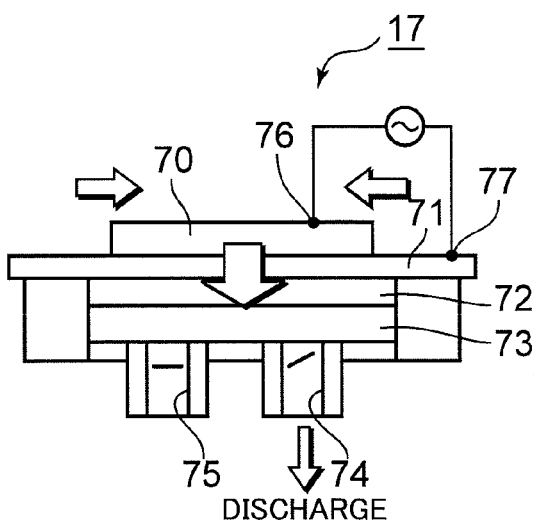
DISCHARGE
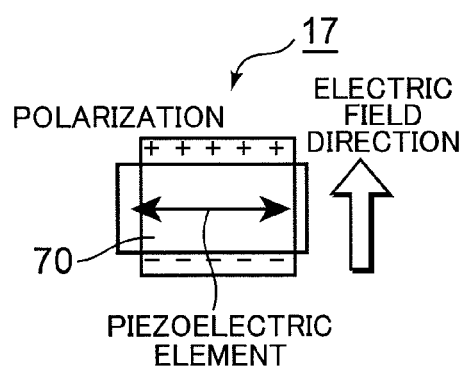
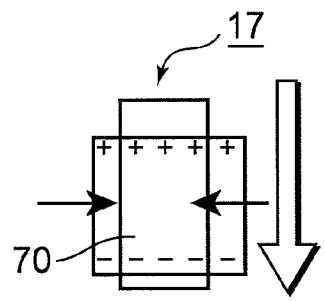

REDUCED WATER MIST GENERATING DEVICE AND ELECTRIC APPARATUS

TECHNICAL FIELD

The present invention relates to a reduced water mist generating device and an electric apparatus.

BACKGROUND ART

Reduced water (for example, hydrogen water or aqueous solution of ascorbic acid) with a reduced component (for example, hydrogen molecules or ascorbic acid) dissolved therein has been used for preventing aging of skin and hair and long-term storage of food.

Patent Document 1 suggests a hydrogen water supply device that can produce reduced water. In the hydrogen water supply device of such kind, part of water that should be supplied into a dwelling is introduced into an electrolysis tank installed outdoors and made containing hydrogen gas and oxygen gas. The water containing hydrogen gas and oxygen gas is then supplied into the dwelling in the form of a mixture with the water that should be supplied into the dwelling.

Thus, in the hydrogen water supply device described in Patent Document 1, water containing hydrogen gas and oxygen gas is supplied into the dwelling in the form of a mixture with the water that should be supplied into the dwelling. However, in order to ensure efficient aging prevention of skin and hair and efficient long-term storage of food, it is desirable that reduced water be delivered to every portion of the object (for example, skin, hair, food).

CITATION LIST

Patent Literature
Patent Document 1: Japanese Patent Application Publication No. 2005-105289

SUMMARY OF INVENTION

It is an object of the present invention to resolve the above-mentioned problem and provide a reduced water mist generating device that can generate and atomize reduced water and supply the atomized reduced water as a reduced water mist, and also to provide an electric apparatus equipped with the reduced water generating device.

The reduced water mist generating device according to one aspect of the present invention includes: a water acquiring section that acquires water for generating reduced water having dissolved therein a reduced component obtained by reducing cations generated by ionization of an acidic component in water; a reduced water generating unit that generates the reduced water from the water acquired by the water acquiring section; and a reduced water atomizing section that atomizes the reduced water generated by the reduced water generating unit to obtain mist-like reduced water.

With such a configuration, water acquired by the water acquiring section is converted by the reduced water generating unit into the reduced water, and the reduced water is atomized by the reduced water atomizing section to obtain mist-like reduced water. Since the mist-like reduced water is in a mist-like state, the reduced water drifts in the space and eventually arrives at the object.

Therefore, it is possible to generate and atomize the reduced water and provide the atomized reduced water as a reduced water mist. As a result, aging of the human skin can be inhibited, skin can be lubricated, and skin inflammation can be reduced. In addition, storage objects such as food can be stored for a long time.

BRIEF DESCRIPTION OF THE DRAWINGS

FIG. 15 illustrate the operation of a pump (pressurizing section).

DESCRIPTION OF EMBODIMENTS

Figure 1:
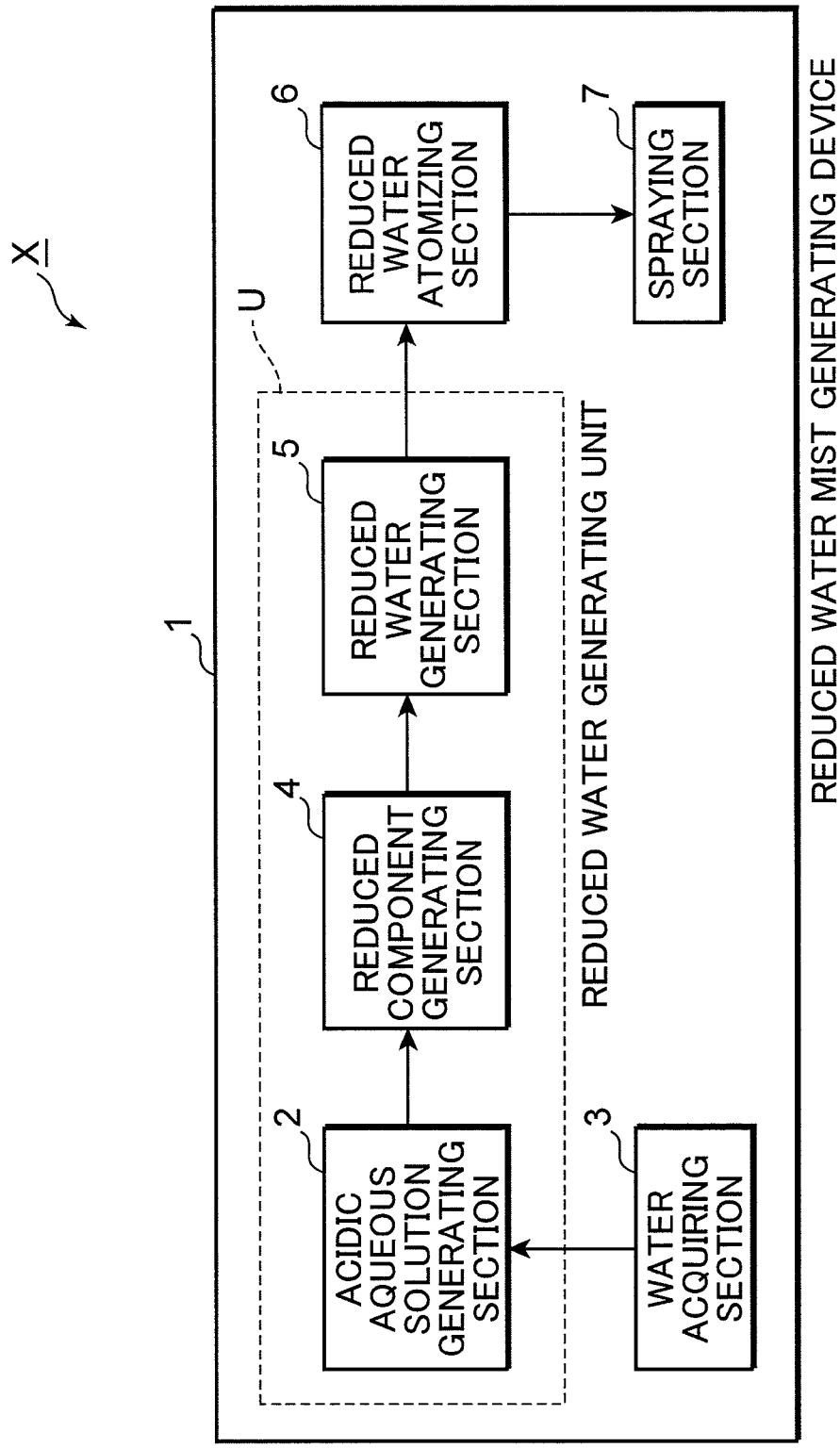
FIG. 1 shows an example of functional configuration of the reduced water mist generating device of one embodiment of the present embodiment.

The reduced water mist generating device according one embodiment of the present invention will be described below. FIG. 1 is a block diagram illustrating an example of a functional configuration of the reduced water mist generating device according to the embodiment of the present embodiment. A reduced water mist generating device 1 shown in FIG. 1 includes a reduced water generating unit U, a water acquiring section 3, a reduced water atomizing section 6, and a spraying section 7.

The reduced water mist generating device 1 is incorporated in a hairdressing-cosmetic device X for use, for example, for either or both of hairdressing and cosmetic applications. The hairdressing-cosmetic device X thus incorporating the reduced water mist generating device 1 is called a hairdressing-cosmetic device incorporating a reduced water mist generating device.

In the reduced water mist generating device 1, a reduced water generating device is constituted by the reduced water generating unit U, water acquiring section 3, and reduced water atomizing section 6.

In the reduced water mist generating device 1, the water acquiring section 3 acquires water for generating reduced water having dissolved therein a reduced component obtained by reducing cations generated by ionization of the below-described acidic component in water. Therefore, the user is not required to replenish water for generating the reduced water.

The reduced water atomizing section 6 produces mist-like reduced water by atomizing the reduced water. The spraying section 7 sprays, as a reduced water mist, the reduced water (mist-like reduced water) atomized by the reduced water atomizing section 6. Therefore, the reduced water can be sprayed in distant locations and within a wide range.

The reduced water generating unit U in the reduced water mist generating device 1 includes an acid aqueous solution generating section 2, a reduced component generating section 4, and a reduced water generating section 5.

In the reduced water generating unit U, the acid aqueous solution generating section 2 generates an acidic component in water and generates an acid aqueous solution containing cations and anions generated by ionization of the acidic component generated in water. Examples of the acidic component include hydrogen peroxide and nitric acid, and where these hydrogen peroxide or nitric acid are dissolved in water, at least hydrogen ions are generated as cations.

The reduced component generating section 4 generates a reduced component by supplying electrons and reducing the cations contained in the acidic aqueous solution. Thus, since the acidic component is ionized in the acidic aqueous solution, the acidic aqueous solution contains at least cations generated from the acidic component. When the acidic component is hydrogen peroxide or nitric acid, the cations generated from the acidic component are hydrogen ions. In this case, the reduced component generating section 4 supplies electrons and reduces the hydrogen ions generated from the hydrogen peroxide or nitric acid ionized by dissolution in the acidic aqueous solution and generates hydrogen molecules as the reduced component.

In the reduced water generating section 5, the reduced component generated by the reduced component generating section 4 is dissolved in water to generate reduced water having the reduced component dissolved therein. In the present embodiment, the reduced water is hydrogen water.

Various specific configurations of the reduced water mist generating device of one embodiment of the present embodiment will be described below.

(Specific Configurations of Reduced Water Mist Generating Device)

Figure 2:
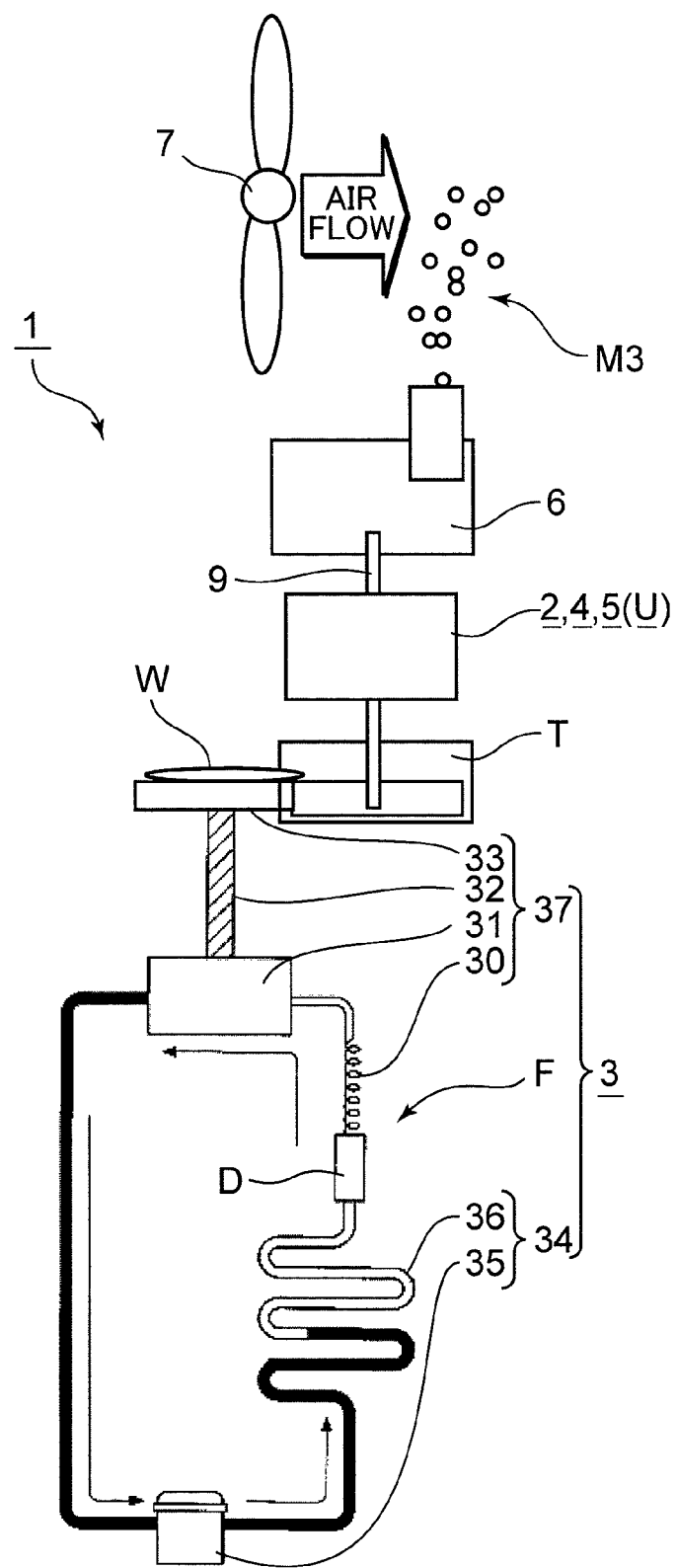
FIG. 2 shows the specific configuration example 1 of the reduced water mist generating device of one embodiment of the present embodiment.

FIG. 2 shows the specific configuration example 1 of the reduced water mist generating device of one embodiment of the present embodiment.

SPECIFIC CONFIGURATION EXAMPLE 1

In the reduced water mist generating device 1 shown in FIG. 2, the water acquiring section 3 includes a heat radiating section 34 that compresses refrigerant gas to a high-temperature and high-pressure state and then causes heat radiation to obtain refrigerant liquid, and a cooling section 37 that depressurizes the refrigerant liquid and then evaporates the refrigerant liquid to obtain refrigerant gas. Thus, the water acquiring section 3 includes a heat exchanger having the heat radiating section 34 and the cooling section 37.

In such water acquiring section 3, the heat radiating section 34 and the cooling section 37 are provided in a refrigeration cycle section F. The heat radiating section 34 is provided with a compressor 35 that compresses the refrigerant gas to a high-temperature and high-pressure state and a condenser 36 in which the refrigerant gas at a high temperature and under a high pressure is cooled by heat radiation and refrigerant liquid is obtained.

The cooling section 37 is provided with an expansion valve 30 that depressurizes the refrigerant liquid dried by a drier D to facilitate gasification of the refrigerant liquid, an evaporator 31 that gasifies the depressurized refrigerant liquid to obtain refrigerant gas, a heat conducting member 32 provided in contact with the evaporator 31, and a dew condensation water generating section 33 provided in contact with the heat conducting member 32. The heat conducting member 32 is constituted by a pillar-like member with good thermal conductivity such as that of a metal, as shown in FIG. 2.

In such cooling section 37, the dew condensation water generating section 33, heat conducting member 32, and evaporator 31 are thermally connected, and the cooling effect of the evaporator 31 reaches the dew condensation water generating section 33 via the heat conducting member 32. As a result, the dew condensation water generating section 33 is cooled, the air around the dew condensation water generating section 33 is cooled, and dew condensation water (simply referred to hereinbelow as "water") W adheres to the surface of the dew condensation water generating section 33. The dew condensation water generating section 33 and the heat conducting member 32 may be formed integrally. The heat conducting member 32 may be also fixedly attached to the dew condensation water generating section 33. Alternatively, the dew condensation water generating section 33 may be in contact with the heat conducting member 32. In any case, the configuration is preferred in which heat can be efficiently exchanged between the dew condensation water generating section 33 and the heat conducting member 32.

Water W generated in the dew condensation water generating section 33 by such cooling section 37 flows into a water tank T and is sucked up into the acidic aqueous solution generating section 2. The water W sucked up into the acidic aqueous solution generating section 2 is converted into reduced water M3 by the reduced water generating unit U, that is, the acidic aqueous solution generating section 2, reduced component generating section 4, and reduced water generating section 5. The reduced water M3 is then atomized by the reduced water atomizing section 6 and sprayed as a reduced water mist by an air flow generated by an air blowing fan constituted as the spraying section 7.

With such water acquiring means 3, water is acquired by condensation of moisture contained in the air by the cooling effect of the cooling section 37. Therefore, the user is not required to replenish water for generating the acidic aqueous solution.

Figure 3:
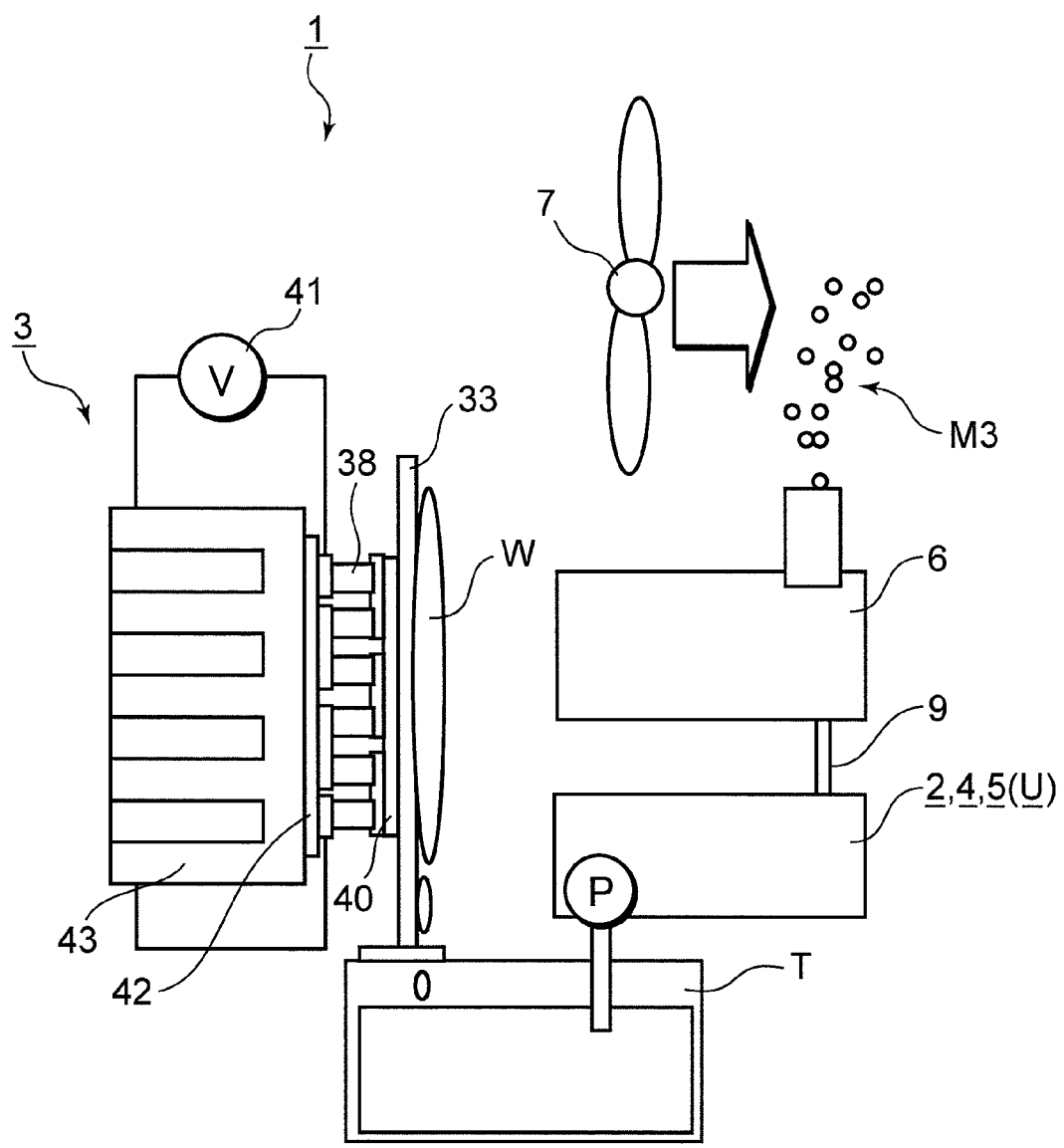
FIG. 3 shows the specific configuration example 2 of the reduced water mist generating device of one embodiment of the present embodiment.

FIG. 3 shows the specific configuration example 2 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 2

In the reduced water mist generating device 1 shown in FIG. 3, the water acquiring section 3 includes a Peltier element 38 that acquires water by condensation of moisture contained in the air through cooling with a cooling surface 40.

The Peltier element 38 has the cooling surface 40 and a heat radiating surface 42. The dew condensation water generating section 33 is attached to the cooling surface 40. The cooling surface 40 and the dew condensation water generating section 33 may be thermally connected. A heat radiating fin 43 is attached to the heat radiating surface 42.

In such water acquiring section 3, when an electric current is supplied to the Peltier element 38 by a power source 41 for the Peltier element, the cooling surface 40 of the Peltier element 38 is cooled and this cooling effect reaches the dew condensation water generating section 33. As a result, the dew condensation water generating section 33 is also cooled, the air surrounding the dew condensation water generating section 33 is cooled, and water W adheres to the surface of the dew condensation water generating section 33. Heat is generated from the heat radiating surface 42 of the Peltier element 38, but this heat is radiated by the heat radiating fin 43.

Water W generated in the dew condensation water generating section 33 by such Peltier element 38 flows into the water tank T and is sucked up into the acidic aqueous solution generating section 2. The water W sucked up into the acidic aqueous solution generating section 2 is converted into the reduced water M3 by the reduced water generating unit U, that is, the acidic aqueous solution generating section 2, reduced component generating section 4, and reduced water generating section 5. The reduced water M3 is then atomized by the reduced water atomizing section 6. The reduced water M3 atomized by the reduced water atomizing section 6 is sprayed as a reduced water mist by an air flow generated by an air blowing fan constituted as the spraying section 7.

With such water acquiring section 3, water can be acquired with the Peltier element 38 that has a small volume and generates no noise or vibrations. Therefore, the water acquiring section 3 can be reduced in size and no noise or vibrations are generating when water is acquired.

Figure 4:
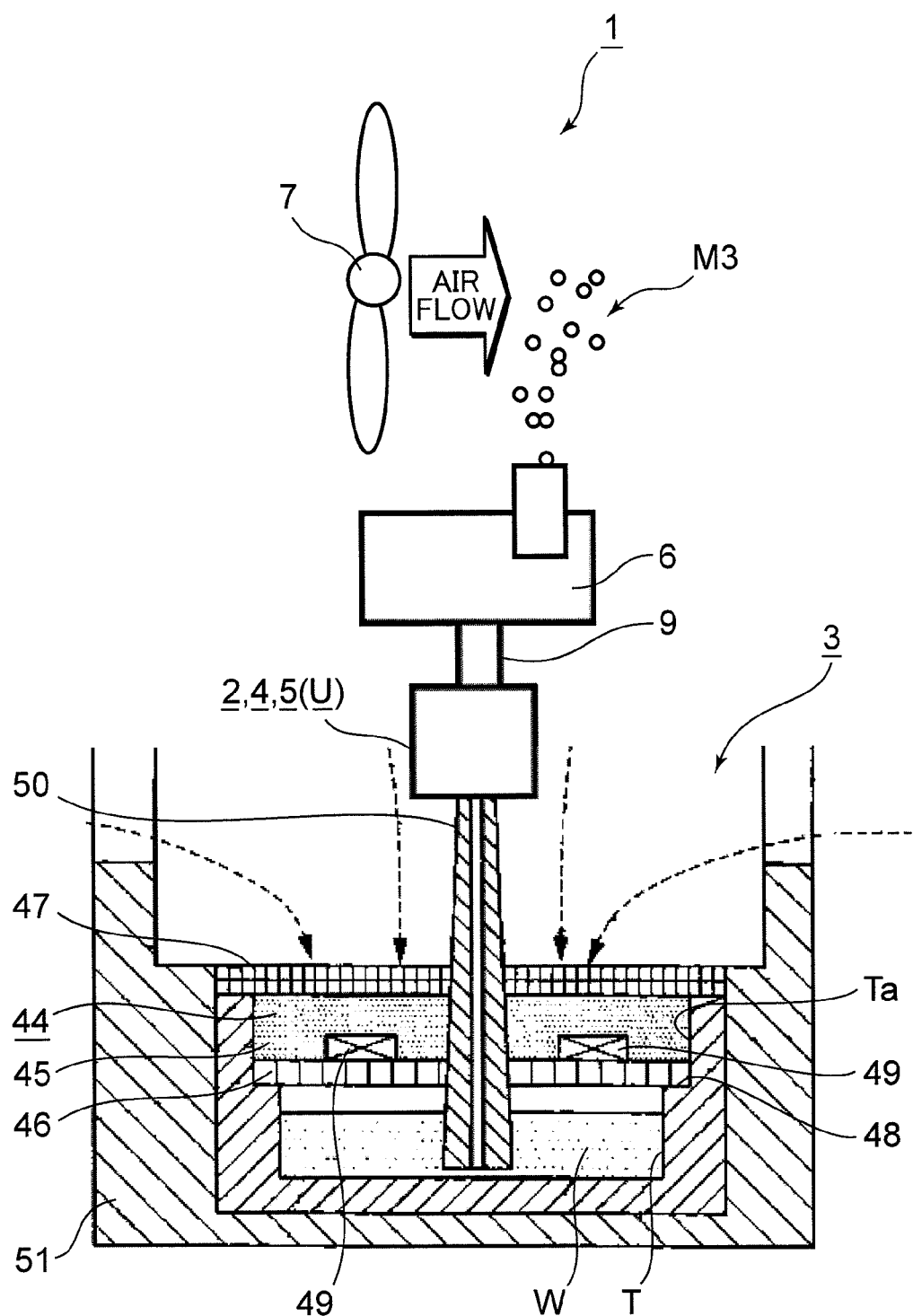
FIG. 4 shows the specific configuration example 3 of the reduced water mist generating device of one embodiment of the present embodiment.

FIG. 4 shows the specific configuration example 3 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 3

In the reduced water mist generating device 1 shown in FIG. 4, the water acquiring section 3 includes an adsorbent 45 that adsorbs moisture contained in the air and a heater 49 that heats the adsorbent 45 and causes desorption of the moisture adsorbed by the adsorbent 45. In this case, the preferred adsorbent 45 is a zeolite.

In such water acquiring section 3, the water tank T from a hard material such as polypropylene is provided in the lower portion inside a housing 51, and an upper opening Ta of the water tank T is closed with an adsorbing body 44.

The adsorbing body 44 is constituted by the adsorbent 45 as the main component thereof, a water-permeable hard rear plate 46 such as a mesh provided on the rear surface side of the adsorbent 45, and a moisture-permeable and water-impermeable film 47 provided on the front surface side of the adsorbent 45. The rear plate 46 is supported by a receiving section 48 provided in the upper opening Ta of the water tank T, the adsorbent 45 is loaded on the rear plate 46, and the upper end of the upper opening Ta is sealed with the film 47. A heater 49 is provided inside the adsorbing body 44.

A water conveying section 50 is inserted through the adsorbing body 44. The upper end of the water conveying section 50 is positioned in the lower portion of the water tank T, and the upper end of the water conveying section 50 is positioned in the upper portion of the housing 51.

The water conveying section 50 has a rod-like shape and is formed from a porous material or has a fine hole for conveying the water stored in the water tank T to the distal end (upper end) by a capillary effect.

In such water acquiring section 3, moisture contained in the air is adsorbed by the adsorbent 45 via the film 47, as shown by a broken-line arrow. The user energizes the heater 49 for a predetermined time interval to desorb moisture from the adsorbent 45 that has adsorbed the moisture contained in the air. Moisture is thus desorbed from the adsorbent 45 heated by the heater 49. The water desorbed from the adsorbent 45 flows from the rear plate 46 into the water tank T and is accumulated therein.

The moisture adsorbed by the adsorbent 45 is thus desorbed as long as the heater 49 is energized. Where the moisture is desorbed, the adsorption ability of the adsorbent 45 is restored correspondingly to the desorbed amount. After the moisture contained in the adsorbent 45 has been desorbed for a predetermined time interval, the user stops energizing the heater 49 to enable adsorption of moisture into the adsorbent 45.

The water W that has thus accumulated in the water tank T is fed to the acidic aqueous solution generating section 2 by the capillary effect in the water conveying section 50. The water W fed to the acidic aqueous solution generating section 2 is converted into reduced water M3 by the reduced water generating unit U, that is, the acidic aqueous solution generating section 2, reduced component generating section 4, and reduced water generating section 5. The reduced water M3 is then atomized by the reduced water atomizing section 6 and sprayed as a reduced water mist by an air flow generated by an air blowing fan constituted as the spraying section 7.

With such a configuration, moisture contained in the air is adsorbed by the adsorbent 45 and the moisture adsorbed by the adsorbent 45 is used to generate the acidic aqueous solution. Therefore, water for generating the acidic aqueous solution can be acquired from the air even without energizing the device. As a result, power consumption can be reduced.

Figure 5:
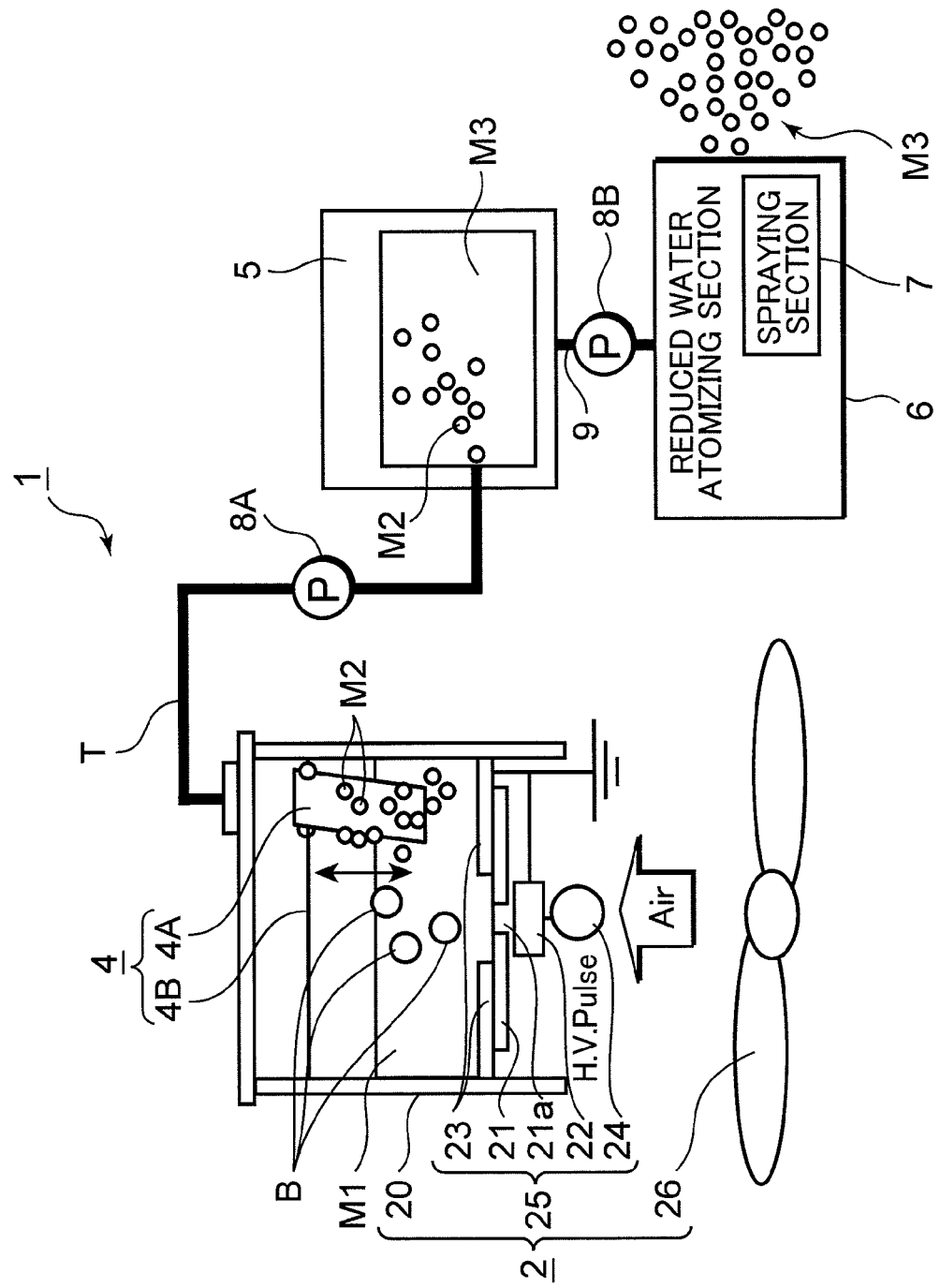
FIG. 5 shows the specific configuration example 4 of the reduced water mist generating device of one embodiment of the present embodiment.

FIG. 5 shows the specific configuration example 4 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 4

The terms "upstream" and "downstream" in the explanation below indicate zones upstream and downstream with respect to the air flow introduced from an blowing section 26.

In the reduced water mist generating device 1 shown in FIG. 5, the acidic aqueous solution generating section 2 is provided with a storage section 20, a discharge section 25, and the air blowing section 26. In such acidic aqueous solution generating section 2, the storage section 20 is also provided as the water acquiring section 3 shown in FIG. 1 and stores water serving as a starting material for an acidic aqueous solution M1 or the acidic aqueous solution M1. Alternatively, water acquired by the water acquiring section 3 provided separately from the storage section 20 may be stored in the storage section 20 as water serving as a starting material for the acidic aqueous solution M1.

The storage section 20 is a tank installed in intimate contact with the downstream side of the discharge section 25, and the internal space of the storage section communicates with a through hole 21a of an insulating spacer 21.

In the acidic aqueous solution generating section 2, the discharge section 25 is formed integrally with the storage section 20 and provided with the insulating spacer 21 having the fine through hole 21a, an upstream electrode (first electrode) 22 disposed upstream of the insulating spacer 21, a downstream electrode (second electrode) 23 disposed downstream of the insulating spacer 21 and constituting part of the bottom portion or wall portion of the storage section 20, and a high-voltage applying section 24 for applying a high voltage to the upstream electrode 22 and the downstream electrode 23, performing a creeping discharge in the through hole 21a of the insulating spacer 21, and generating a starting material of an acidic component in the through hole 21a. In another possible configuration, the first electrode is constituted by the downstream electrode 23, and the second electrode is constituted by the upstream electrode 22.

In such discharge section 25, the insulating spacer 21 is constituted by an insulator such as a ceramic board and placed between the upstream electrode 22 and downstream electrode 23 constituted by a conductor such as a metal. The diameter of the through hole 21a of the insulating spacer 21 is from several tens of microns to about several millimeters, preferably several hundreds of microns. Since the through hole 21a has a very small diameter of about several hundreds of microns, water stored in the storage section 20 is prevented by surface tension from penetrating into the through hole 21a, while the flow of air therethrough is ensured.

Further, the upstream electrode 22 and the downstream electrode 23 are connected to the high-voltage applying section 24. A high voltage for microplasma discharge is applied by the high-voltage applying section 24 to the upstream electrode 22 and the downstream electrode 23. As a result, a creeping discharge is generated in the through hole 21a of the insulating spacer 21 that is sandwiched between the upstream electrode 22 and the downstream electrode 23.

In the acidic aqueous solution generating section 2, the air blowing section 26 is provided upstream of the discharge section 25 and introduces an air flow to the through hole 21a of the insulating spacer 21. As a result, bubbles B that pass from the outside of the storage section 20 to the inside of the storage section 20 via the through hole 21a can be generated in a large amount, and a starting material for an acidic component is generated in a large amount in the through hole 21a where the creeping discharge has been generated by the discharge of the discharge section 25.

The starting material for an acidic component that has been generated in a large amount in the through hole 21a is introduced by the air flow produced by the air blowing section 26 into the storage section 20 that is disposed communicatively with the through section 21a and dissolved in the water stored in the storage section 20.

When the acidic component is the aforementioned hydrogen peroxide or nitric acid, the starting material for an acidic component can be a superoxide radical, a hydroxyl radical, a nitrogen oxide, or a nitric acid ion. When dissolved in the water stored in the storage section 20, such starting materials for an acidic component generate hydrogen peroxide or nitric acid.

Thus, a superoxide radical and hydroxyl radical generate hydrogen peroxide when dissolved in water, and the water stored in the storage section 20 is converted into water having hydrogen peroxide dissolved therein. A nitrogen oxide and nitric acid ion generate nitric acid when dissolved in water, and the water stored in the storage section 20 is converted into water having nitric acid dissolved therein. When the water stored in the storage section 20 is converted into water having hydrogen peroxide or nitric acid dissolved therein, the hydrogen peroxide or nitric acid are ionized into cations and anions and produce water including at least hydrogen ions as cations.

With such acidic aqueous solution generating section 2, the discharge section 25 is disposed upstream of the storage section 20 in a state in which the through hole 21a of the insulating spacer 21 communicates with the storage section 20. Therefore, the discharge section 25 and storage section 20 can be formed integrally in a compact manner and the entire device 1 can be reduced in size.

Further, since the starting material of an acidic component that has been generated in a large amount is dissolved in the water contained in the storage section 20, the acidic component is generated at a high concentration in the water contained in the storage section 20. As a result, the acidic component present at a high concentration in the water contained in the storage section 20 is ionized and the acidic aqueous solution M1 is generated in which at least hydrogen ions are contained at a high concentration as cations.

In the reduced water mist generating device 1 shown in FIG. 5, the reduced component generating section 4 includes a reducing substance 4A that is constituted by an element that is higher in ionization tendency than hydrogen, and reduces the hydrogen ions contained in the acidic aqueous solution M1 to generate hydrogen molecules as the reduced component, and an adjusting section 4B that adjusts the amount of generated hydrogen molecules.

In the present embodiment, the reducing substance 4A in the reduced component generating section 4 is zinc. In addition to zinc, substances that are constituted by elements that are higher in ionization tendency than hydrogen can be also used as the reducing substance 4A. The reducing substance 4A is detachably attached to the adjusting section 4B, and the adjusting section 4B has a function of adjusting the range in which the reducing substance 4A is immersed in the acidic aqueous solution M1. In the present embodiment, the adjusting section 4B is an adjusting rod that can move up and down in the inner space of the storage section 20. However, the adjusting section 4B is not limited to the configuration that moves up and down in the inner space of the storage section 20.

In other words, a mechanism that can adjust the range in which the reducing substance 4A is immersed in the acidic aqueous solution M1 can be used as the adjusting section 4B. For example, the range in which the reducing substance 4A is immersed in the acidic aqueous solution M1 can be adjusted by rotating the adjusting section 4B and adjusting the angle between the reducing substance 4A and the surface of the acidic aqueous solution M1. The adjusting section 4B may be rotated manually or with a motor.

In such reduced component generating section 4, the range in which the reducing substance (zinc) 4A is immersed in the acidic aqueous solution M1 changes following the movement of the adjusting section (adjusting rod) 4B in the vertical direction in the inner space of the storage section 20.

Within the range in which the reducing substance (zinc) 4A is immersed into the acidic aqueous solution M1, the hydrogen ions contained in the acidic aqueous solution M1 are reduced. Thus, within the range in which the reducing substance (zinc) 4A is immersed into the acidic aqueous solution M1, the acidic component supplies electrons to the hydrogen ions that have been generated by ionization in the acidic aqueous solution M1 and zinc ions are produced. As a result, the hydrogen ions accept electrons and become hydrogen atoms, and the hydrogen atoms are bonded by two to form hydrogen molecules.

With such reduced component generating section 4, hydrogen ions contained at a high concentration in the acidic aqueous solution M1 can be easily reduced and hydrogen molecules can be generated as the reduced component M2. Further, since the generated amount of hydrogen molecules that are generated on the basis of the hydrogen ions contained at a high concentration can be easily and freely adjusted, hydrogen water having a hydrogen concentration within a wide range can be easily generated as the reduced water M3.

In the reduced water mist generating device 1 shown in FIG. 5, a reduced component supply tube T is led out from a position corresponding to that substantially immediately above the reducing substance 4A in the storage section 20, and the reduced water generating section 5 is connected by the reduced component supply tube T. In this case, since the specific gravity of hydrogen molecules, which are the reduced component M2, is significantly less than that of the air, the hydrogen molecules rise substantially above the reducing substance 4A. This is why the reduced component supply tube T takes the hydrogen molecules out from substantially immediately above the reducing substance 4A, as mentioned hereinabove.

A pump 8A is provided in the reduced component supply tube T, and this pump 8A pumps the reduced component M2 to the reduced water generating section 5. As a result, the reduced component M2 is introduced into the reduced water generating section 5 and the reduced water M3 is generated.

Further, in the reduced water mist generating device 1 shown in FIG. 5, a reduced water supply tube 9 is led out of the reduced water generating section 5, and the reduced water atomizing section 6 is connected by the reduced water supply tube 9. A pump 8B is provided in the reduced water supply tube 9, and the pump 8B pumps the reduced water M3 to the reduced water atomizing section 6. The reduced water atomizing section 6 atomizes as a mist the reduced water M3 pumped out by the pump 8B from the reduced water generating section 5. The reduced water M3 atomized by the reduced water atomizing section 6 is sprayed as a reduced water mist by the spraying section 7.

With such reduced water mist generating device 1, the reduced water M3 is generated if the processing of generating the acidic aqueous solution M1, the processing of supplying electrons to the cations contained in the acidic aqueous solution M1 generated by the aforementioned processing, reducing the cations, and generating the reduced component, and the processing of dissolving the reduced component generated by the aforementioned processing in water are performed successively. Therefore, the reduced water M3 can be generated in a simple manner.

Where the object is only to generate the reduced water M3 in the reduced water mist generating device 1 shown in FIG. 5, the reduced water atomizing section 6 and the reduced water supply tube 9 provided between the reduced water atomizing section 6 and the reduced water generating section 5 and having the pump 8B may be omitted.

In this respect, in the conventional configuration, (see Patent Document 1), water is introduced into an electrolytic tank installed outdoors, water including hydrogen gas and oxygen gas is obtained, and this water is thereafter mixed with water that should be supplied into the dwelling to obtain hydrogen water.

Thus, with the conventional configuration, a route for supplying water into the dwelling and an electrolytic tank installed outdoors are used. As a result, a compact configuration for generating hydrogen water cannot be obtained. Further, since the route for supplying water into the dwelling and the outdoor electrolytic tank are used on a large scale, hydrogen water cannot be generated in a simple manner.

By contrast, with the reduced water mist generating device 1 according to the present embodiment, the entire device 1 can have a compact configuration, as mentioned hereinabove. Therefore, the device can be incorporated in products such that can be normally carried by the user, for example, such as a facial massager or sauna suit. Further, with the reduced water mist generating device 1 according to the present embodiment, the reduced water M3 can be generated in a simple manner as mentioned hereinabove.

Figure 6:
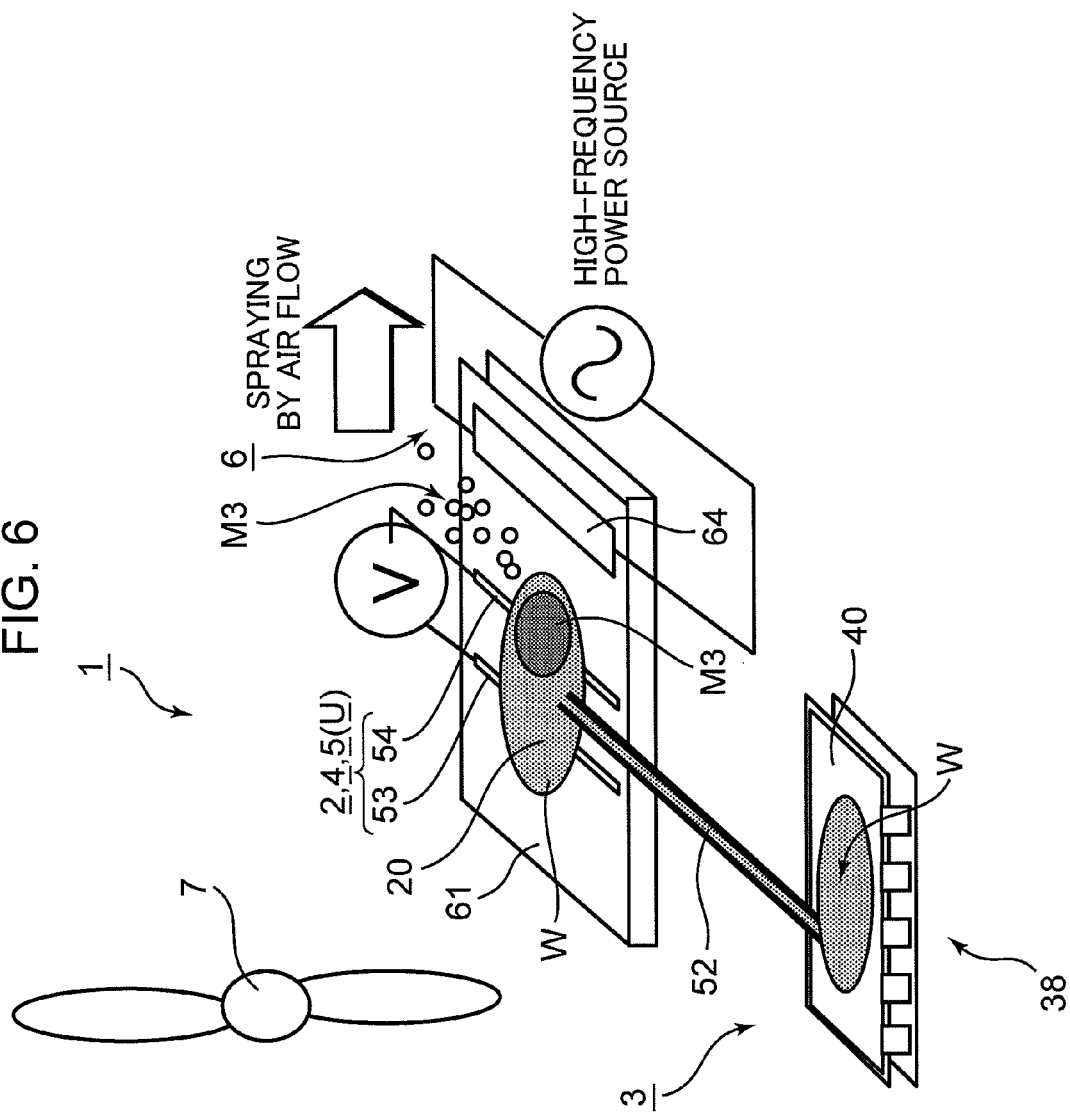
FIG. 6 shows the specific configuration example 5 of the reduced water mist generating device of one embodiment of the present embodiment.

FIG. 6 shows the specific configuration example 5 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 5

In the reduced water mist generating device 1 shown in FIG. 6, the reduced water atomizing section 6 includes a surface acoustic wave generating section 64 that generates a surface acoustic wave and atomizes the reduced water M3 by the surface acoustic wave. Such surface acoustic wave generating section 64 is constituted by an oscillator provided at one end of one surface of a substrate 61 and connected to a high-frequency power source. When the oscillator oscillates in the surface acoustic wave generating section 64, the oscillation wave propagates as a surface acoustic wave on the one surface of the substrate 61.

On the other end of the one surface of the substrate 61, a concave water reservoir section (reduced water storage section) 20 is provided, and an anode 53 and a cathode 54 immersed in the water W in a state in which the water W has accumulated in the water reservoir section 20 is provided in the water reservoir section 20. The anode 53 and cathode 54 have a function of electrolyzing the water W that has accumulated in the water reservoir section 20 and generating reduced water (in this case, hydrogen water) M3 on the cathode 54 side. In other words, the anode 53 and cathode 54 consolidate the functions of the above-described reduced water generating unit U, that is, the acidic aqueous solution generating section 2, reduced component generating section 4, and reduced water generating section 5.

Further, in such reduced water mist generating device 1, the water acquiring section 3 is constituted by the Peltier element 38, and when the Peltier element 38 is energized, the cooling effect produced by the cooling section 40 of the Peltier element 38 causes condensation of moisture contained in the air, thereby acquiring the water W.

The acquired water W moves through a capillary tube 52 under the capillary effect and is supplied to the water reservoir section 20 on the substrate 61. The water W may be also fed to the water reservoir section 20 under gravity.

With such reduced water mist generating device 1, the water W acquired by energizing the Peltier element 38 is electrolyzed by the anode 53 and cathode 54 and the reduced water M3 (in this case, hydrogen water) is obtained on the cathode 54 side. The reduced water M3 is atomized by the surface acoustic waves generated by the surface acoustic waves generating section 64 and propagating over the substrate 61 and the reduced water mist (mist-like reduced water) is obtained. The reduced water mist is sprayed by the air blowing fan configured as the spraying section 7.

With such reduced water mist generating device 1, the surface acoustic waves from the surface acoustic waves generating section 64 propagate on the surface of the substrate 61 and reach the surface of the reduced water M3 stored in the concave water reservoir section 20. As a result, the reduced water M3 is atomized by the surface acoustic waves.

Since the reduced water M3 is thus atomized as a result of the surface acoustic waves propagating over the surface of the substrate 61 and reaching the surface of the reduced water M3, it is clear that the oscillation surface where the surface acoustic waves propagate is at the same level as the surface of the reduced water M3. Therefore, the configuration of the reduced water atomizing section 6 can be reduced in size and the reduced water mist generating device 1 can be made compact.

In such reduced water mist generating device 1, the water acquiring section 3 is not limited to the configuration in which the water W is acquired by energizing the Peltier element 38. For example, The configuration using the cooling section of a heat exchanger that is explained in Specific Configuration Example 1 and the configuration using the effect of moisture adsorption by the adsorbent 45 that is explained in Specific Configuration Example 2 can be also used.

Figure 7:
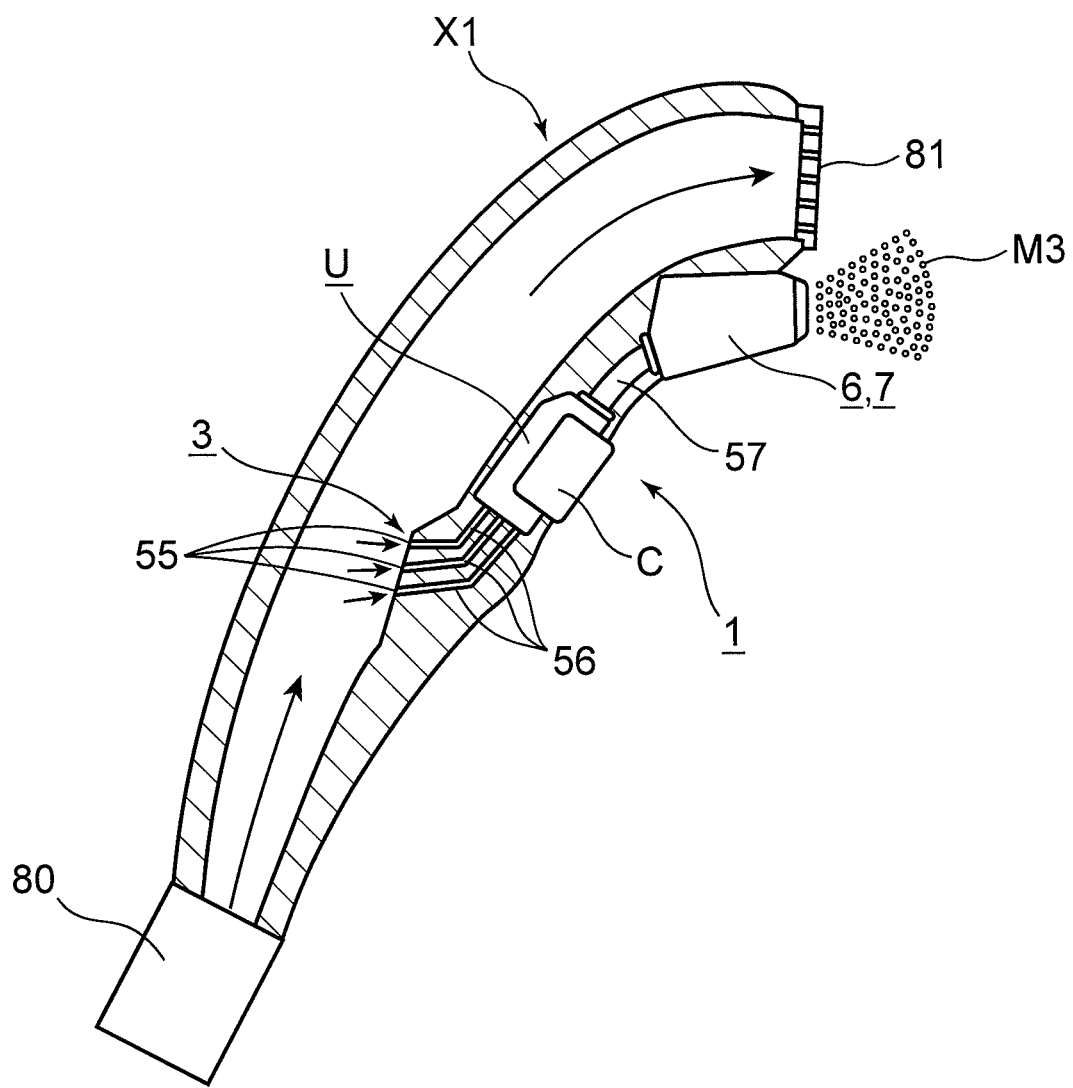
FIG. 7 shows the specific configuration example 6 of the reduced water mist generating device of one embodiment of the present embodiment.

FIG. 7 shows the specific configuration example 6 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 6

The reduced water mist generating device 1 shown in FIG. 7 is incorporated in a shower head X1, which is a hairdressing-cosmetic device. The shower head X1 constitutes a hairdressing-cosmetic device of a type incorporating a reduced water mist generating device in which the reduced water mist generating device 1 is incorporated. The shower head X1 discharges tap water supplied via a water supply hose 80 in the form of a shower from a discharge port 81.

The reduced water mist generating device 1 is provided with a plurality of openings 55 and water supply tube 56 corresponding to each of the plurality of openings 55 as the water acquiring section 3. In the water acquiring section 3, each water supply tube 56 passes through to the reduced water generating unit U, and water for generating the reduced water M3 is supplied to the reduced water generating unit U via the water supply tubes 56.

Further, in the reduced water mist generating device 1, an ascorbic acid cartridge C loaded with ascorbic acid is attached to the reduced water generating unit U so that the reduced water M3 generated by the reduced water generating unit U can flow into the cartridge under the pressure created by the tap water supplied to the water supply tubes 56 and then return to the reduced water generating unit U. The ascorbic acid may be in a solid state, which is the original state thereof, or in a state of aqueous solution. However, since ascorbic acid is soluble in water, the powdered form thereof is preferred.

The reduced water M3 generated by the reduced water generating unit U flows into the ascorbic acid cartridge C. In this case, the reduced water M3 is an aqueous ascorbic acid solution in which ascorbic acid has been dissolved.

The reduced water mist generating device 1 is provided with the reduced water atomizing section 6 and spraying section 7, and the reduced water M3 produced as an aqueous ascorbic acid solution is atomized and sprayed by the atomizing section 6 and spraying section 7.

In such shower head X1, when tap water is supplied into the shower head X1 through the water supply hose 80, part of the tap water flows into the water supply tubes 56 via the openings 55, as shown by solid-line arrows. The tap water that flowed into the water supply tubes 56 flows into the reduced water generating unit U to be converted into the reduced water M3.

The reduced water M3 generated by the reduced water generating unit U flows into the ascorbic acid cartridge C under the pressure of tap water that flowed into the water supply tubes 56, the ascorbic acid loaded into the ascorbic acid cartridge C is dissolved, and an aqueous ascorbic acid solution is obtained. The reduced water M3 in the form of aqueous ascorbic acid solution returns into the reduced water generating unit U under the pressure of tap water that flows into the ascorbic acid cartridge C.

The reduced water M3 in the form of the aqueous ascorbic acid solution that has returned into the reduced water generating unit U passes through a water feed tube 57 under the pressure of tap water that has flown into the water supply tubes 56 and flows into the reduced water atomizing section 6. The reduced water M3 that flowed into the reduced water atomizing section 6 is atomized and sprayed as a reduced water mist by the spraying section 7.

Thus, part of the tap water supplied into the shower head X1 through the water supply hose 80 is sprayed as the reduced water M3 in the form of aqueous ascorbic acid solution and the remaining tap water is discharged by a discharge port 81. Therefore, the user can shower the body with tap water discharged as a shower and also shower the body with the reduced water M3. Therefore, cosmetic and health improving effects can be obtained (for example, the immune strength of the person is increased, collagen is generated, common cold is prevented or rapid recovery is ensured, resistance to stress is increased, and generation of carcinogenic substances is inhibited).

Figure 8:
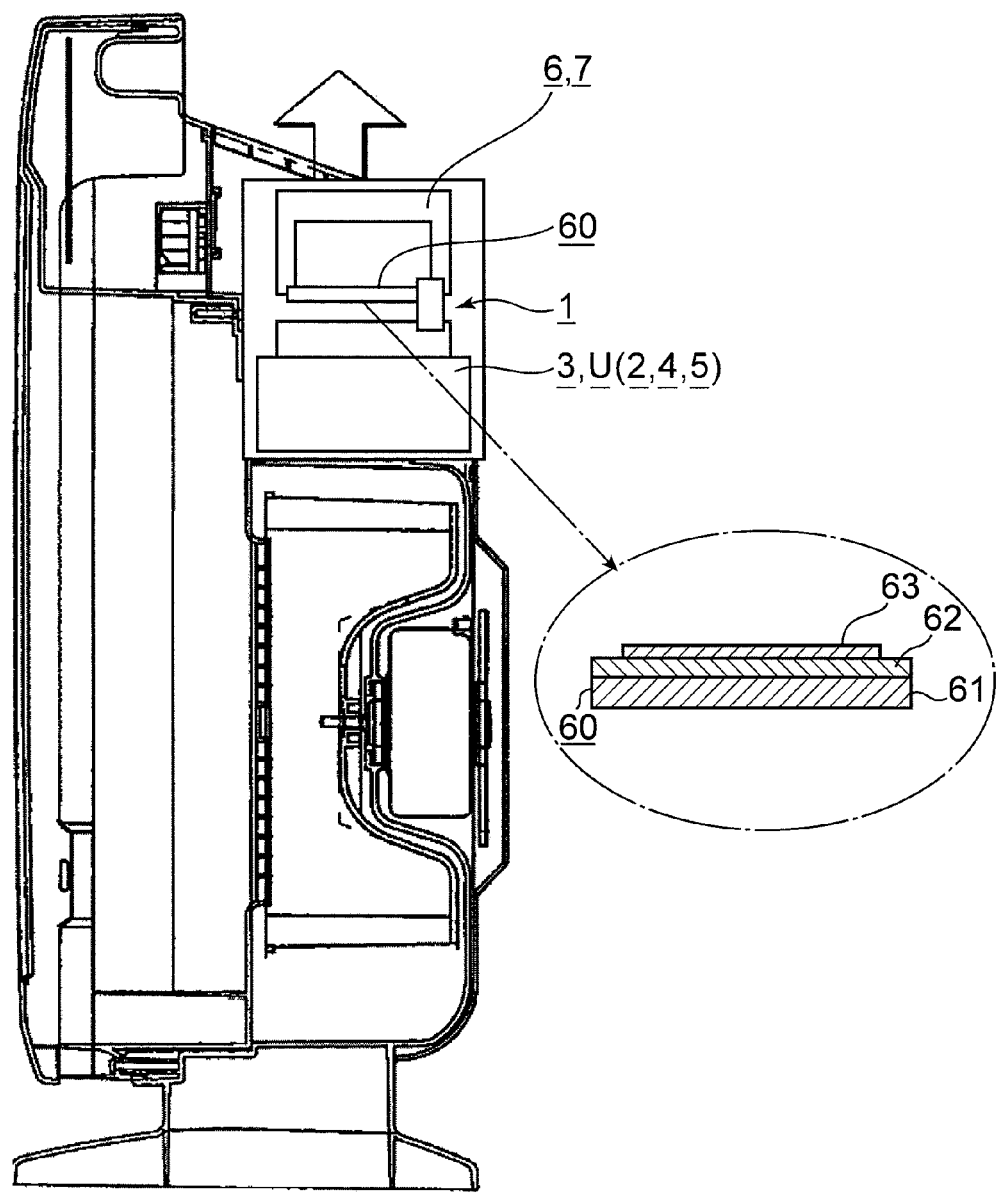
FIG. 8 shows the specific configuration example 7 of the reduced water mist generating device of one embodiment of the present embodiment.

FIG. 8 shows the specific configuration example 7 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 7

In the reduced water mist generating device 1 shown in FIG. 8, the reduced water atomizing section 6 includes an ultrasound wave emitting element 60 that atomizes the reduced water M3 by emitting ultrasound waves therein. The ultrasound wave emitting element 60 includes a substrate 61, a thermal insulating layer 62, and a heat generating body 63.

In the ultrasound wave emitting element 60, the substrate 61 is for example a silicon substrate. The thermally insulating layer 62 is formed on one surface side in the thickness direction of the substrate 61 and composed of a porous silicon layer with a thermal conductivity sufficiently less than that of the substrate 61. The heat generating layer 63 is formed on the thermally insulating layer 62 and composed of a thin metal film (for example, thin gold film) with thermal conductivity and electric conductivity higher than those of the thermally insulating layer 62.

In the ultrasound wave emitting element 60, ultrasound waves are generated by heat exchange between the heat generating body 63 and a medium (for example, the air) that proceeds when the heat generating body 63 is energized by an alternating electric current.

In such ultrasound wave emitting element 60, the reduced water M3 generated by the reduced water generating unit 5 is irradiated with ultrasonic waves. As a result, the surface of the reduced water M3 is successively atomized and therefore liquid droplets of a nanometer diameter can be sprayed as a reduced water mist.

Figure 9:
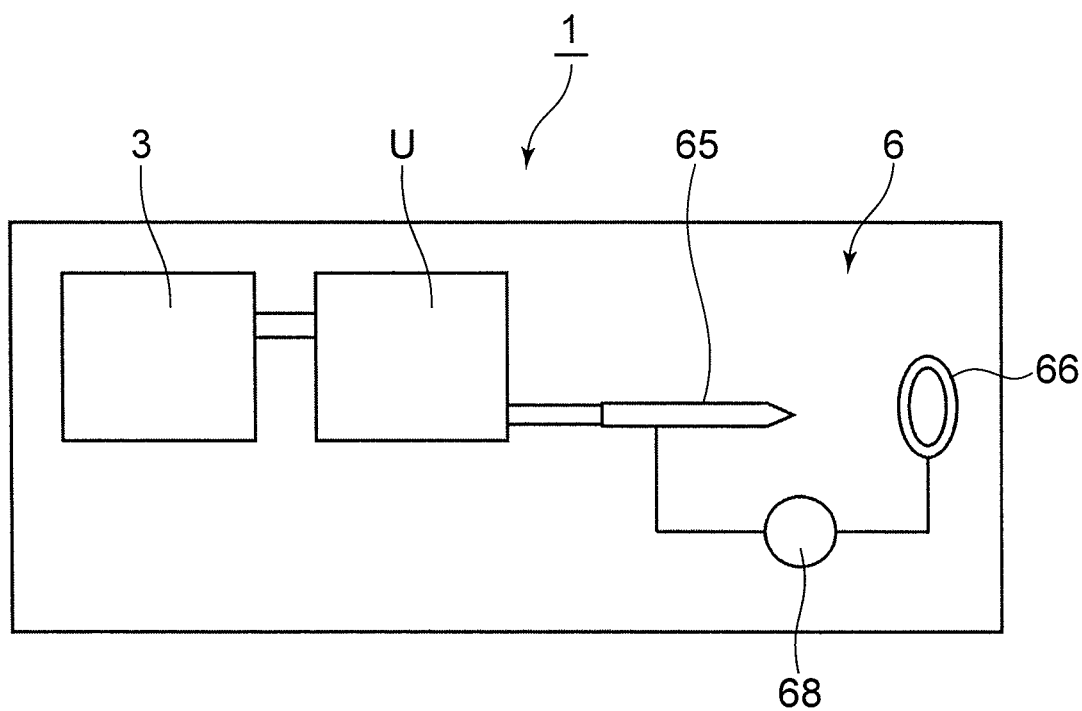
FIG. 9 shows the specific configuration example 8 of the reduced water mist generating device of one embodiment of the present embodiment.
Figure 10:
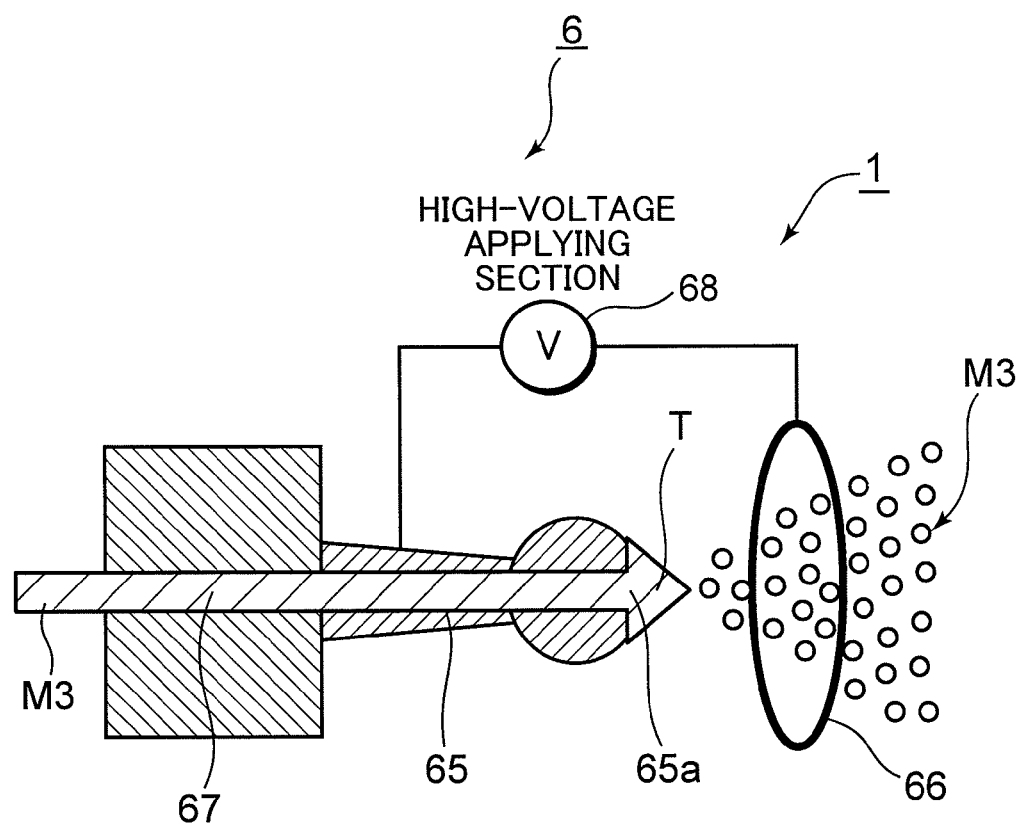
FIG. 10 shows the specific configuration example 8 of the reduced water mist generating device of one embodiment of the present embodiment.

FIG. 9 and FIG. 10 show the specific configuration example 8 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 8

In the reduced water mist generating device 1 shown in FIG. 9, the water acquired by the water acquiring section 3 is converted into the reduced water by the reduced water generating unit U. The reduced water is then atomized by the reduced water atomizing section 6. The reduced water atomizing section 6 includes a discharge electrode 65, a counter electrode 66, and a high-voltage applying section 68 that applies a high voltage to the discharge electrode 65.

In the reduced water atomizing section 6, the reduced water generated by the reduced water generating unit U is supplied to the tip of the discharge electrode 65, and a high voltage is applied from the high-voltage applying section 68 to the reduced water supplied to the tip of the discharge electrode 65. As a result, nanosize reduced water mist M3 including radicals is generated.

FIG. 10 is a detail view illustrating an example configuration of the reduced water atomizing section 6. The reduced water atomizing section 6 further includes a reduced water supply tube 67 that supplies the reduced water M3 to the distal end portion 65a of the discharge electrode 65. In such reduced water atomizing section 6, the reduced water M3 that has flown into the reduced water feed tube 67 is fed to the distal end portion 65a of the discharge electrode 65 through the reduced water supply tube 67.

When a high voltage is supplied between the discharge electrode 65 and the counter electrode 66 by the high-voltage applying section 68 in a state in which the reduced water M3 is thus supplied to the discharge electrode 65, an electric field is generated between the discharge electrode 65 and the counter electrode 66 and an electric charge is accumulated in the reduced water M3 supplied to the distal end portion 65a of the discharge electrode 65.

As a result, a Coulomb force acts between the counter electrode 66 and the reduced water M3 supplied to the distal end portion 65a of the discharge electrode 65, and the surface of the reduced water M3 locally rises conically. The zone in which the surface of the reduced water M3 has locally risen conically is a Taylor cone T.

Where the Taylor cone T is thus formed, electric charges concentrate at the tip of the Taylor cone T, the intensity of electric field at the tip of the Taylor cone T increases, and the Coulomb force generated at the tip of the Taylor cone T increases. As a result, the Taylor cone T further grows.

Where the Taylor cone T thus grows, electric charges concentrate at the tip of the Taylor cone T, and the electric charge density rises therein, the reduced water M3 located in the tip portion of the Taylor cone T receives large energy (repulsion force of electric charges that have concentrated to a high density) and undergoes repeated fragmentation and scattering (Rayleigh fragmentation) under the effect of forces surpassing the surface tension. As a result, the mist-like reduced water M3 having a nanosize diameter is generated in a large amount.

With such reduced water mist generating device 1, droplets of a nanosize diameter can be scattered in a large amount in the form of a reduced water mist. In the reduced water mist generating device 1 shown in FIG. 9, an electrostatic atomizing section is constituted by the discharge electrode 65 and counter electrode 66, but providing the counter electrode 66 is not a mandatory condition and the electrostatic atomizing section may be also constituted only by the discharge electrode 65. In this case, an electric discharge is also generated at the discharge electrode 65 and the electrostatically atomized reduced water M3 is scattered toward a casing (not shown in the figure) or the like.

Figure 11:
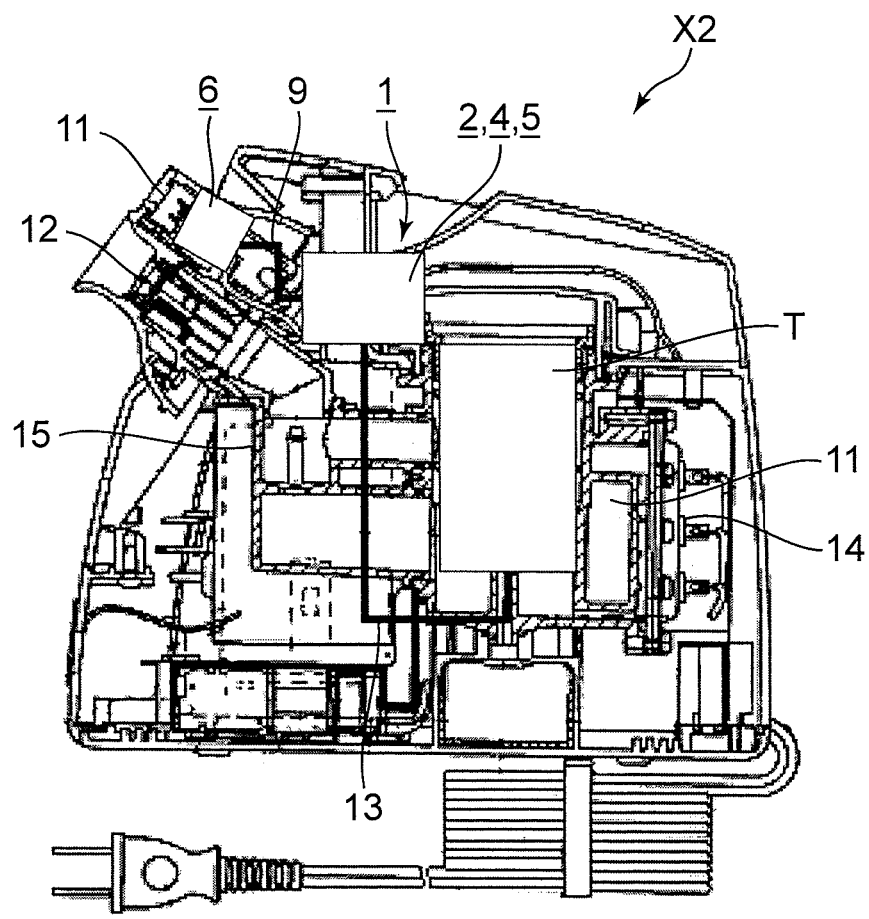
FIG. 11 shows the specific configuration example 9 of the reduced water mist generating device of one embodiment of the present embodiment.

FIG. 11 shows the specific configuration example 9 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 9

The reduced water mist generating device 1 shown in FIG. 11 is incorporated in a facial massager (electric apparatus) X2. A hairdressing-cosmetic device incorporating a reduced water mist generating device is configured by incorporating the reduced water mist generating device 1 in the facial massager X2.

The facial massager X2 is provided with one reduced water mist nozzle 11 releasing the reduced water M3 as a reduced water mist and one steam nozzle 12 releasing steam.

More specifically, when steam is released, water stored in a water tank T is fed to a boiler 11 connected to the water tank T, and then heated and evaporated with a heater 14. The boiler 11 is connected to a steam passage 15. The steam generated by the boiler 11 is fed to the steam nozzle 12 via the steam passage 15 and discharged from the steam nozzle 12.

Where a reduced water mist is scattered, water stored in the water tank T of the facial massager X2 is fed by a water supply tube 13 to the reduced water generating unit U, that is, to the acidic aqueous solution generating section 2, reduced component generating section 4, and reduced water generating section 5 and reduced water M3 is generated. The generated reduced water M3 is fed by the reduced water supply tube 9 to the reduced water atomizing section 6 and atomized. The atomized reduced water M3 is discharged from the reduced water mist nozzle 11.

Figure 12:
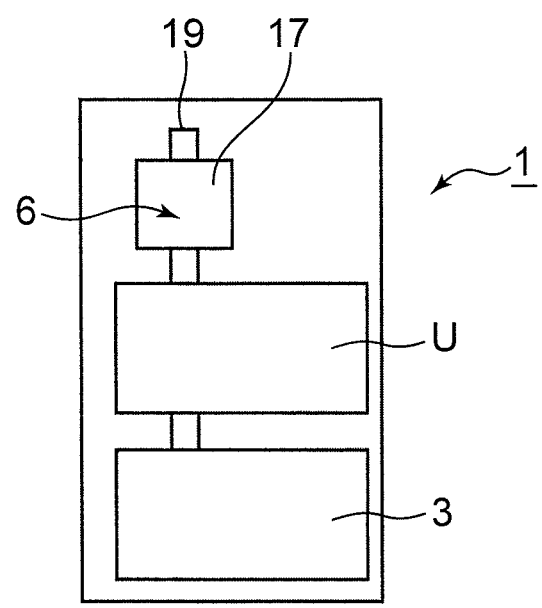
FIG. 12 shows the specific configuration example 10 of the reduced water mist generating device of one embodiment of the present embodiment.

FIG. 12 shows the specific configuration example 10 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 10

In the reduced water mist generating device 1 shown in FIG. 12, the reduced water atomizing section 6 includes a pressurizing section 17 that pressurizes liquid, and a mist is obtained by applying pressure to the liquid and spraying the liquid through a small hole 19. In such reduced water mist generating device 1, water acquired by the water acquiring section 3 is converted into the reduced water M3 by the reduced water generating unit U, and the reduced water M3 is pressurized by the pressurizing section 17 and sprayed from the small hole 19. As a result, the reduced water M3 is converted into a mist-like reduced water mist.

Figure 13:
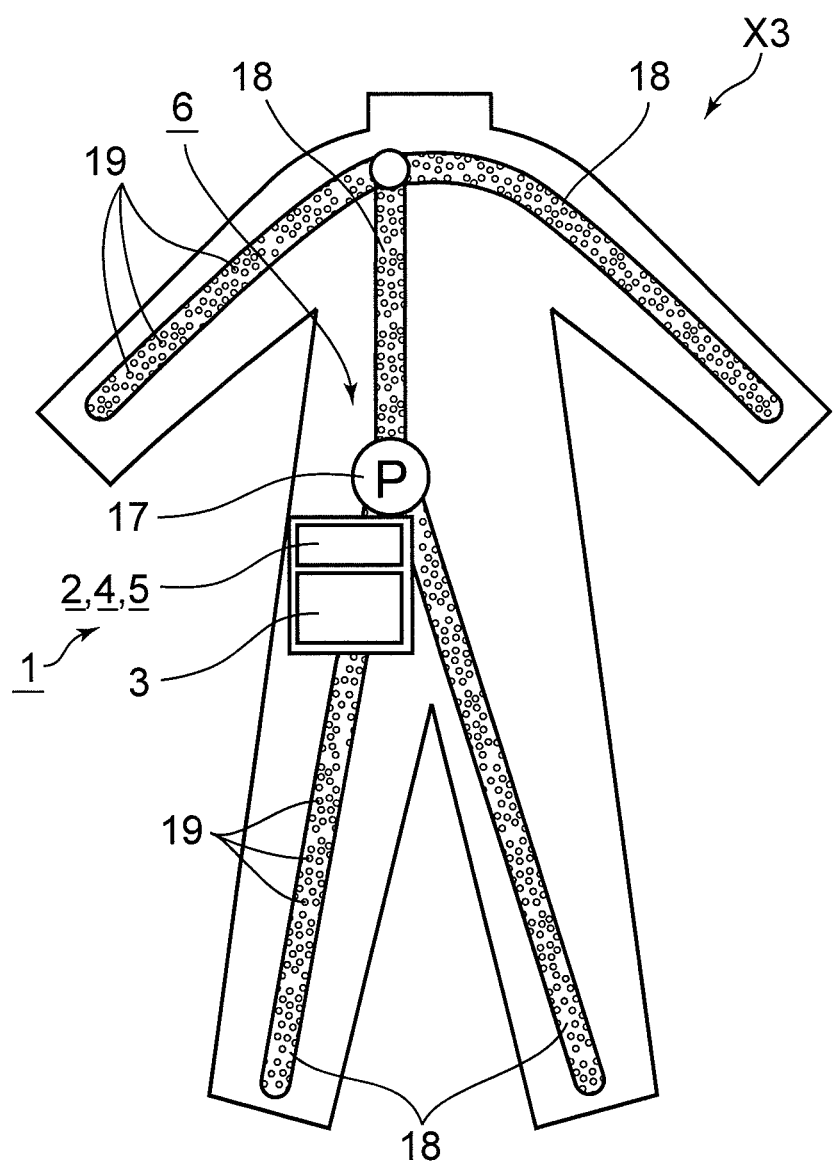
FIG. 13 shows the specific configuration example 11 of the reduced water mist generating device of one embodiment of the present embodiment.

FIG. 13 shows the specific configuration example 11 of the reduced water mist generating device of one embodiment of the present embodiment. In this figure, the elements identical to those of the reduced water mist generating device 1 shown in FIG. 2 are assigned with reference numerals identical to those shown in FIG. 2. Explanation of these elements is herein omitted.

SPECIFIC CONFIGURATION EXAMPLE 11

In the reduced water mist generating device 1 shown in FIG. 13 is incorporated in a sauna suit X3 which is a hairdressing-cosmetic device. A hairdressing-cosmetic device incorporating a reduced water mist generating device is configured by incorporating the reduced water mist generating device 1 in the sauna suit X3.

In the sauna suit X3, a pump (pressurizing section) 17 that pressurizes the reduced water M3 and a plurality of small holes 19 for ejecting the reduced water M3 pressurized by the pump 17 constitute the reduced water atomizing section 6.

In the reduced water mist generating device 1, water W obtained by the water acquiring section 3 is converted into the reduced water M3 by the reduced water generating unit U, that is, the acidic aqueous solution generating section 2, reduced component generating section 4, and reduced water generating section 5. The reduced water M3 is then supplied by the pump 17 to a pipe 18 stretched inside the sauna suit X3. The reduced water M3 supplied to the pipe 18 is sprayed through the plurality of small holes 19 provided in the pipe 18.

With such a configuration, the reduced water M3 can be atomized in a large amount and scattered as a reduced water mist.

SPECIFIC CONFIGURATION EXAMPLE 12

Figure 14A:
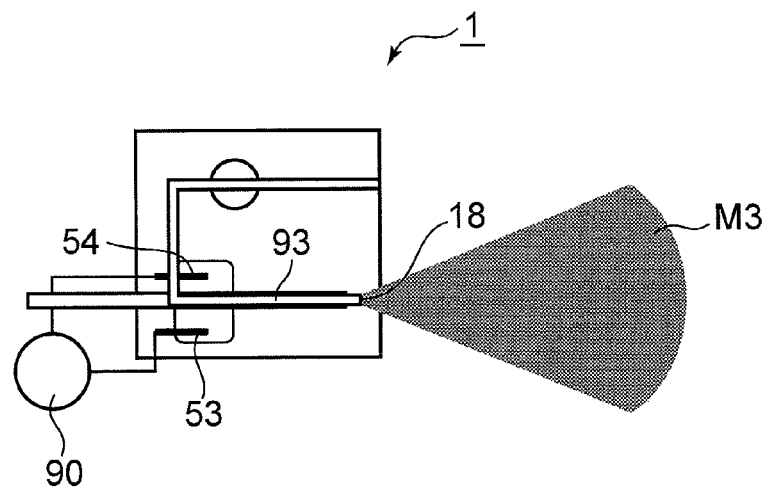
FIG. 14 show the specific configuration example 12 of the reduced water mist generating device of one embodiment of the present embodiment.
Figure 14B:
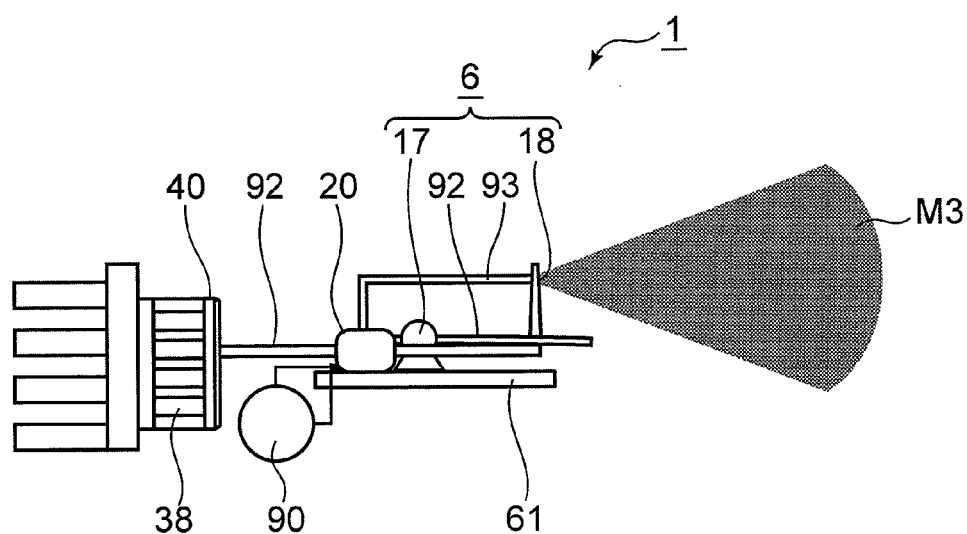

FIGS. 14A, 14B illustrate a specific configuration example 12 of the reduced water mist generating device of one embodiment of the present invention. FIG. 14A is a top view of the reduced water mist generating device. FIG. 14B is a side view of the reduced water mist generating device.

In the reduced water mist generating device 1 shown in FIGS. 14A, 14B, the reduced water atomizing section 6 includes a pressurizing section (pump) 17 that pressurizes the reduced water M3 and a plurality of small holes 18 for ejecting the reduced water M3 pressurized by the pump 17.

When the Peltier element 38 is energized in the reduced water mist generating device 1 shown in FIGS. 14A, 14B, the cooling effect of the cooling surface 40 of the Peltier element 38 causes condensation of moisture contained in the air around the cooling surface 40 and dew condensation water (water W) is obtained. This water W is fed by a capillary action to the water reservoir portion 20 on the substrate 61 via a capillary tube 92. In this case, the dew condensation water (water W) generated by the cooling surface 40 may be fed to the water reservoir portion 20 under gravity.

The water W fed to the water reservoir portion 20 is electrolyzed by an electrolysis section 90 constituted by the anode 53 and cathode 54, and hydrogen water is generated as the reduced water M3. The generated reduced water M3 is fed to the pump 17 via the capillary tube 92 by the capillary effect. In this case, the reduced water M3 generated by the electrolysis section 90 may be fed to the pump 17 under gravity.

The reduced water M3 fed to the pump 17 is pressurized, fed to the small hole 18 via a pressurized water tube 93, and scattered as the mist-like reduced water M3 (reduced water mist) from the small hole 18. With such reduced water mist generating device 1, the reduced water M3 can be atomized in a large amount.

FIGS. 15A, 15B illustrates the operation of the pump (pressurizing section) 17. FIG. 15A illustrates the operation performed when the reduced water M3 is sucked in, and FIG. 15B illustrates the operation performed when the reduced water M3 is discharged.

In the pump 17 shown in FIGS. 15A, 15B, electrodes 76 and 77 are attached to the upper and lower surfaces of a piezoelectric element 70, and an alternating current source is connected to the electrodes 76 and 77. When a voltage is applied to the electrodes 76 and 77, an electric field is generated in the thickness direction of the piezoelectric element 70.

When the direction of the electric field coincides with the polarization direction of the piezoelectric element 70, as shown in FIG. 15B, the piezoelectric element 70 extends in the thickness direction and contracts in the radial direction. As a result, the deflection of a drive diagram 72 decreases. By contrast, when the direction of the electric field is opposite to the polarization direction of the piezoelectric element 70, as shown in FIG. 15A, the piezoelectric element extends in the radial direction thereof and contracts in the thickness direction. As a result, the deflection of the drive diaphragm 72 increases.

Accordingly, plus and minus polarity of the electrodes 76 and 77 is switched alternately to orient the electric field along the polarization direction of the piezoelectric element 70 or in the opposite direction. Since the alternating current source is connected to the electrodes 76 and 77, the polarity is switched automatically.

Where the direction of electric field is thus alternately switched between the polarization direction of the piezoelectric element 70 and the opposite direction, the drive diaphragm 72 vibrates in the thickness direction. The vibrations of the drive diaphragm 72 are transferred to the driven diaphragm (not shown in the figure). As a result, the volume of space 73 fluctuates.

When the volume of space 73 increases as shown in FIG. 15A, the pressure inside the space 73 decreases. Therefore, a valve located inside a suction tube 75 is opened and the reduced water M3 is sucked in. However, when the volume of space 73 decreases, as shown in FIG. 15B, the pressure inside the space 73 increases. Therefore, a valve located inside a discharge tube 74 is opened and the reduced water M3 is discharged.

The operations of sucking in the reduced water M3 via the suction tube 75 and discharging the reduced water M3 via the discharge tube 74 are thus repeated by switching the direction of magnetic field generated in the piezoelectric element 70. Therefore, in the reduced water mist generating device 1 shown in FIGS. 14A, 14B, it is possible to pressurize the reduced water M generated by electrolysis of water remaining in the water reservoir section 20 and discharge the reduced water to the pressurized water tube 93.

Various usage mode of the reduced water mist generating device of one embodiment of the present invention will be explained below.

(Usage Mode of Reduced Water Mist Generating Device)
[Usage Mode 1]

Figure 16:
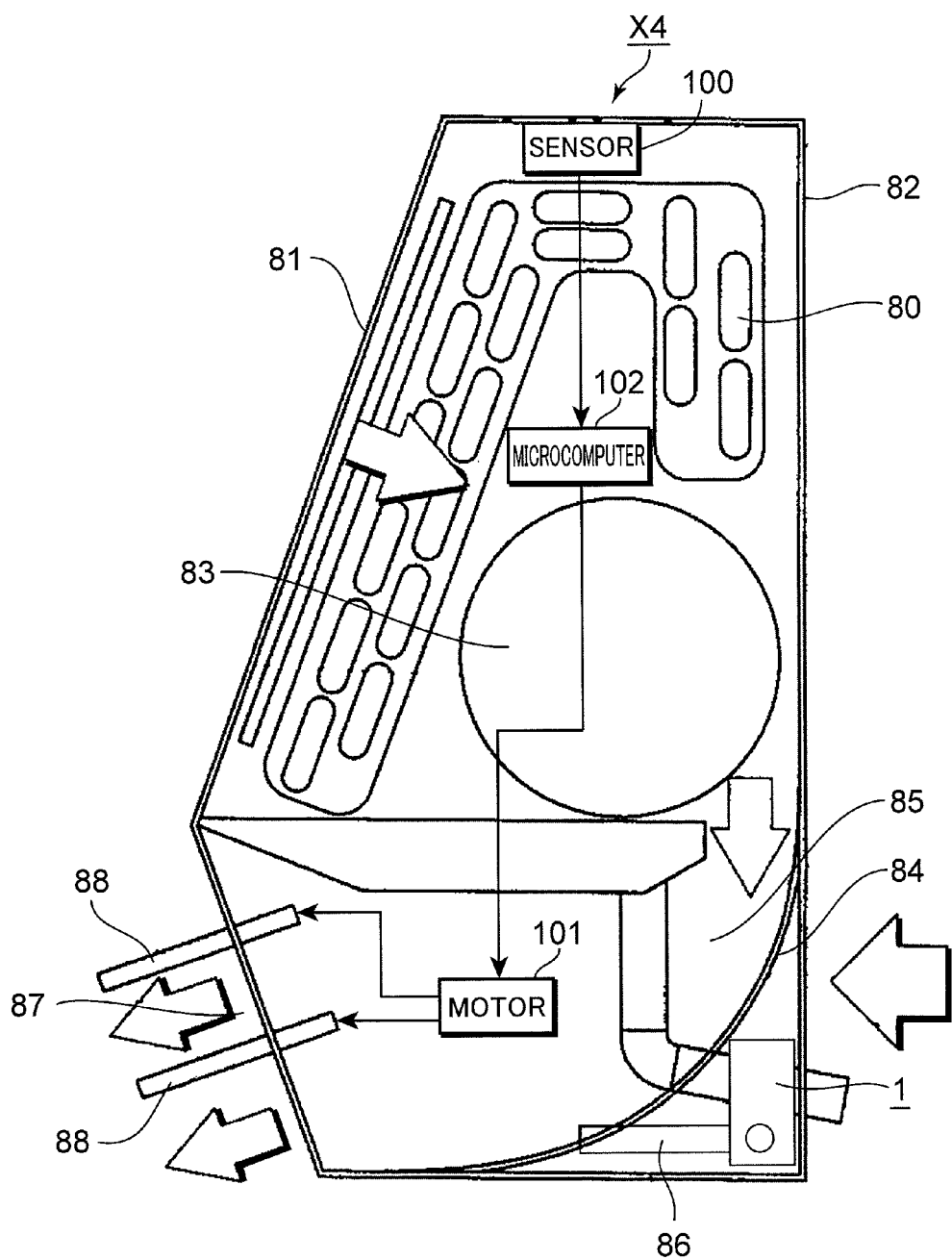
FIG. 16 shows the usage mode 1 of the reduced water mist generating device according to one embodiment of the present invention.

FIG. 16 illustrates a usage mode 1 of the reduced water mist generating device of one embodiment of the present embodiment. An air conditioning device (electric apparatus) X4 shown in FIG. 16 is used as an air conditioner, and the reduced water mist generating device 1 is incorporated therein as a reduced water mist spraying device.

In such air conditioning device X4, an air suction port 81 is provided in the upper portion of the front surface of a housing 82. Further, an air blow-out port 87 provided with a louver 88 is provided in the lower portion of the front surface of the housing 82.

The louver 88 rotates in the left-right direction and up-down direction with respect to the housing 82 about a portion of the housing 82 side as a center, thereby setting the direction in which the air is released from the air blow-out port 87.

A heat exchanger 80 and a fan 83 formed by a transverse flow fan are installed inside the housing 82.

Further, a partition wall 84 for forming an air flow path 85 from the air suction port 81 to the air blow-out port 87 via the fan 83 is provided inside the housing 82.

The lower rear portion inside the housing 82 is separated by the partition wall 84 from the air flow path 5 and serves as a dead space to be used when a drain pipe 89 for draining water is drawn out to the outside from the right end or left end of the housing 82.

The reduced water mist generating device 1 is disposed in this dead space. A reduced water mist feed-out tube 86 is led from the reduced water mist generating device 1 to the air blow-out port 87. In this configuration, one end of the reduced water mist feed-out tube 86 may be opened along the louver 88 in the air blow-out port 87. The mist-like reduced water M3 is sprayed as a reduced water mist from the air blow-out port 87.

In the air conditioning device X4, a plurality of human body detecting sensors (detecting sections) 100 that detect the presence of a human body are provided in appropriate locations outside the housing 82. From the standpoint of detecting a human body and actuating the opening of the louver 88 in the human body direction where the human body is present in front, on the left side, or on the right side of the air conditioning device X4, it is preferred that the human body detecting sensors 100 be provided on the front surface, left side surface, and right side surface of the housing 82.

Further, the air conditioning device X4 includes a motor 101 that actuates the louver 88 and also a microcomputer 102 that controls the entire air conditioning device X4, in particular, the motor 101.

As mentioned hereinabove, the louver 88 rotates in the left-right direction and up-down direction with respect to the housing 82 about a portion of the housing 82 side as a center, thereby setting the direction in which the air is released from the air blow-out port 87. As a result, the air from the air blow-out port 87 is released in the direction set by the louver 88.

The operation of such air conditioning device X4 will be described below. When human body detecting sensors 100 do not detect a human body, the opening of the louver 88 is controlled so as to face forward with respect to the front surface of the housing 82. From the standpoint of facilitating the delivery of the mist-like reduced water M3 sprayed from the air blow-out port 87 to the entire space, it is preferred that the opening of the louver 88 face upward with respect to the front surface of the housing 82.

Since the delivery of the mist-like reduced water M3 to the entire space is facilitated, the reduced water M3 is diffused and scattered to the entire space. In this case, an antioxidation effect is produced on any object article located within the space.

Where the human body detecting sensor 100 detects a human body, the louver 88 is moved so that the opening thereof faces in the direction where the human body is present. In this case, the reduced water M3 is spayed in the direction in which the human body is present. For example, when the human body detecting sensors 100 are present on the front surface, left side surface, and right side surface of the housing 82, the louver 88 can be controlled so that the opening thereof faces forward, to the left, or to the right with respect to the front surface of the housing 82, and the mist-like reduced water M3 can be sprayed in the respective direction. Thus, the air conditioning device X4 can automatically detect the presence of a human body and spray the mist-like reduced water M3 with pinpoint accuracy in the direction in which the human body is present.

Further, since the reduced water M3 can be sprayed only to the limited region within the space, a large amount of the reduced water M3 can be sprayed to the object article with pinpoint accuracy. The louver 88 may be also operated manually. In this case, a similar effect can be also obtained.

The air conditioning device X4 preferably incorporates the reduced water mist generating device 1 (see FIG. 6) spraying a reduced water mist by surface acoustic waves or the reduced water mist generating device 1 (see FIGS. 14A, 14B) obtaining the reduced water M3 from water generated by the Peltier element 38 and ejecting the reduced water M3 from the small hole 18.

These reduced water mist generating devices 1 are known to be compact and lightweight. As a result, the air conditioning device X4 can be reduced in size and weight.

Figure 17:
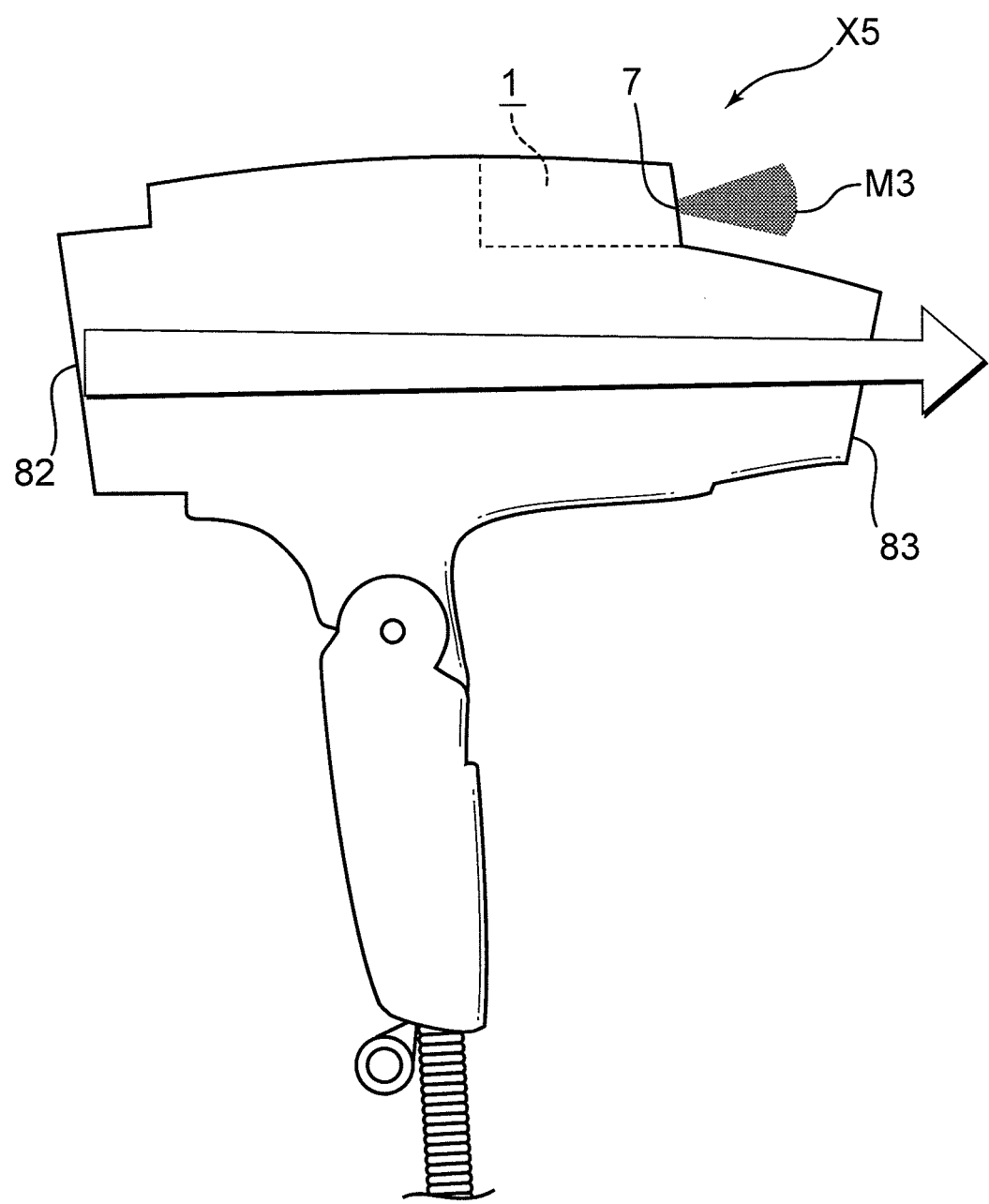
FIG. 17 shows the usage mode 2 of the reduced water mist generating device according to one embodiment of the present invention.

FIG. 17 illustrates the usage mode 2 of the reduced water mist generating device of one embodiment of the present invention.

[Usage Mode 2]

The reduced water mist generating device 1 shown in FIG. 17 is incorporated in a hair drier (electric apparatus) X5 which is a hairdressing-cosmetic device. The hair drier X5 constitutes a hairdressing-cosmetic device of a type incorporating a reduced water mist generating device, wherein the reduced water mist generating device 1 is incorporated.

The hair drier X5 is a hair care device of a type incorporating a reduced water mist generating device obtained by incorporating the reduced water mist generating device 1 as a reduced water mist spraying device in a hair care device for hair treatment.

The hair drier X5 is provided with a suction port 82 through which the external air is sucked in and a discharge port 83 for discharging the heated air. After the external air has been sucked in and heated, the heated air is introduced as an air flow shown by the arrow in the figure. In the reduced water mist generating device 1, the spraying section 7 is configured to spray the reduced water M3 in the direction parallel to the air flow.

With such reduced water mist generating device 1, the reduced water M3 is sprayed as a reduced water mist in the direction parallel to the air flow created by the hair drier X5. The resultant effect is that the high-concentration reduced water is sprayed in a large amount onto the hair. Therefore, the hair drier X5 can spray a large amount of reduced water mist onto the hair, while drying the hair.

Figure 18:
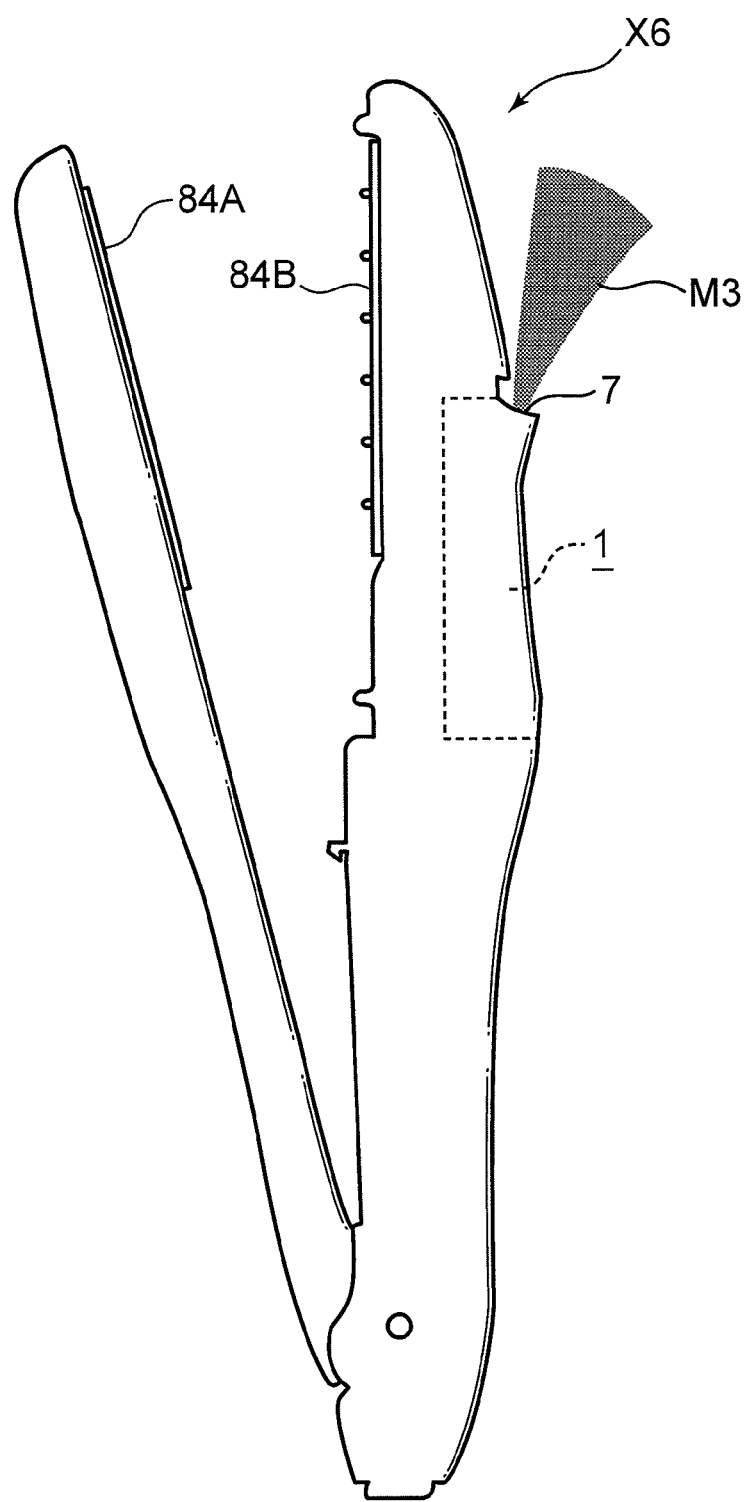
FIG. 18 shows the usage mode 3 of the reduced water mist generating device according to one embodiment of the present invention.

FIG. 18 illustrates the usage mode 3 of the reduced water mist generating device of one embodiment of the present invention.

[Usage Mode 3]

The reduced water mist generating device 1 shown in FIG. 18 is incorporated in a hair iron (electric apparatus) X6 which is a hairdressing-cosmetic device. The hair iron X6 constitutes a hairdressing-cosmetic device of a type incorporating a reduced water mist generating device, wherein the reduced water mist generating device 1 is incorporated.

The hair iron X6 is a hair care device of a type incorporating a reduced water mist generating device obtained by incorporating the reduced water mist generating device 1 as a reduced water mist spraying device in a hair care device for hair treatment.

The hair iron X6 includes a pair of iron plates 84A, 84B that come into contact with the human hair and heat the hair that is in contact therewith. In such hair iron X6, the reduced water M3 is sprayed as a reduced water mist by the spraying section 7 on the hair, while the hair is being heated by the pair of iron plates 84A, 84B. As a result, the hair iron X6 can spray a large amount of the reduced water mist onto the hair, heating the hair and removing curls therefrom.

Figure 19:
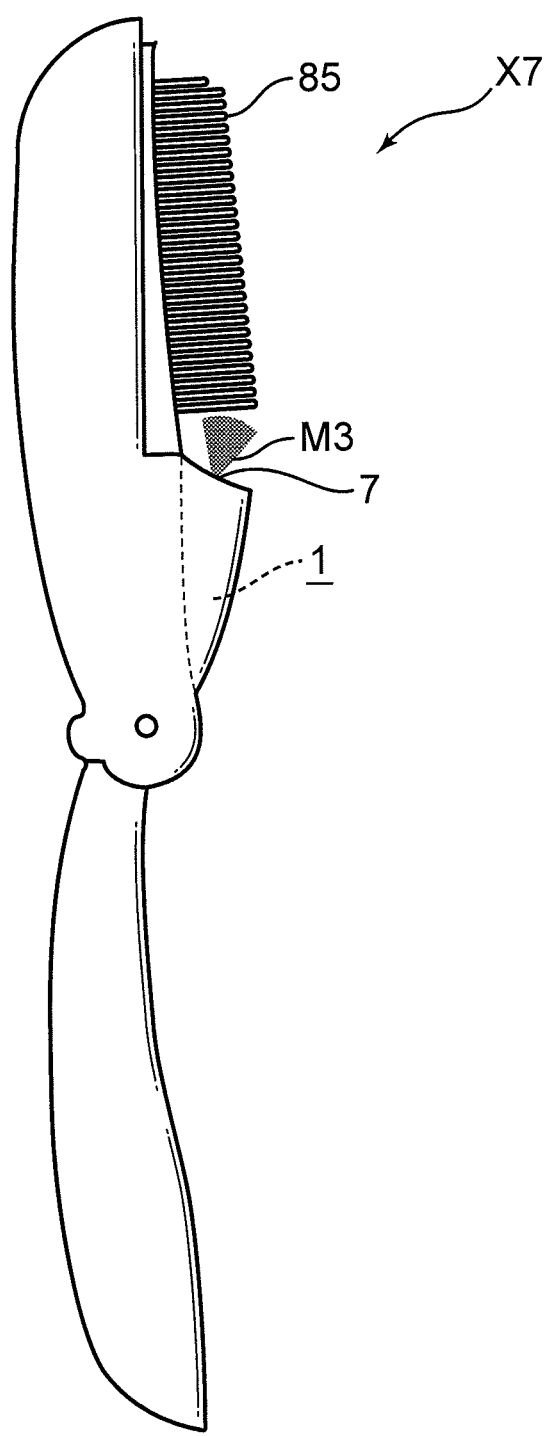
FIG. 19 shows the usage mode 4 of the reduced water mist generating device according to one embodiment of the present invention.

FIG. 19 illustrates the usage mode 4 of the reduced water mist generating device of one embodiment of the present invention.

[Usage Mode 4]

The reduced water mist generating device 1 shown in FIG. 19 is incorporated in a hair brush X7 which is a hair care device. The hair brush X7 constitutes a hairdressing-cosmetic device of a type incorporating a reduced water mist generating device, wherein the reduced water mist generating device 1 is incorporated.

The hair brush X7 is a hair care device of a type incorporating a reduced water mist generating device obtained by incorporating the reduced water mist generating device 1 as a reduced water mist spraying device in a hair care device for hair treatment.

The hair brush X7 is a hair care device for hair treatment and includes a brush 85 for combing the human hair. In such hair brush X7, the reduced water M3 is sprayed as a reduced water mist by the spraying section 7 on the hair, while the hair is being brushed by the brush 85.

As mentioned hereinabove, where the reduced water mist generating device 1 is incorporated in a hair care device, the mist-like reduced water M3 having an antioxidation capability and demonstrating a reducing effect is directly sprayed onto the hair. As a result, the hair is coated with negative ions as in the conventional technique (see Japanese Patent Application Publication No. 2002-191426). In addition, the hair can be provided with gloss and lubrication, hair oxidation can be prevented, and hair growth and restoration can be efficiently enhanced.

The shower head X1, facial massager X2, sauna suit X3, hair drier X5, hair iron X6, and hair brush X7, that is, the so-called hairdressing-cosmetic devices, preferably incorporate the reduced water mist generating device 1 (see FIG. 6) spraying the reduced water M3 by surface acoustic waves. The reduced water mist generating device 1 in which the reduced water M3 is sprayed by surface acoustic waves is known to be compact and lightweight. As a result, the hairdressing-cosmetic devices can be reduced in size and weight.

Further, the reduced water mist generating device 1 of the present embodiment can be provided in a variety of devices such as a sauna device and a unit bath.

Various embodiments in which the reduced water mist generating device 1 of one embodiment of the present invention is used for storing fresh food and flowers or growing plants will be explained below. As described below, the reduced water M3 can be uniformly sprayed onto every portion of the object and such spraying can demonstrate the following effects.

With the conventional technique (see Japanese Patent Application Publication No. 2004-192944), negative ions having antioxidation capacity and positive ions having bactericidal capacity are generated at a ratio of 2:1. However, with such a technique, the antioxidation effect produced by the negative ions is but an indirect effect accompanied by neutralization by positive ions, which results in reduced antioxidation capacity.

By contrast, with the reduced water mist generating device 1 of one embodiment of the present invention, the mist-like reduced water M3 having antioxidation capacity and demonstrating a reducing effect is sprayed directly on the object. Therefore, the antioxidation capacity higher than that attained with negative ions as in the conventional technique can be demonstrated. At the same time, a reducing effect can be obtained.

Figure 20:
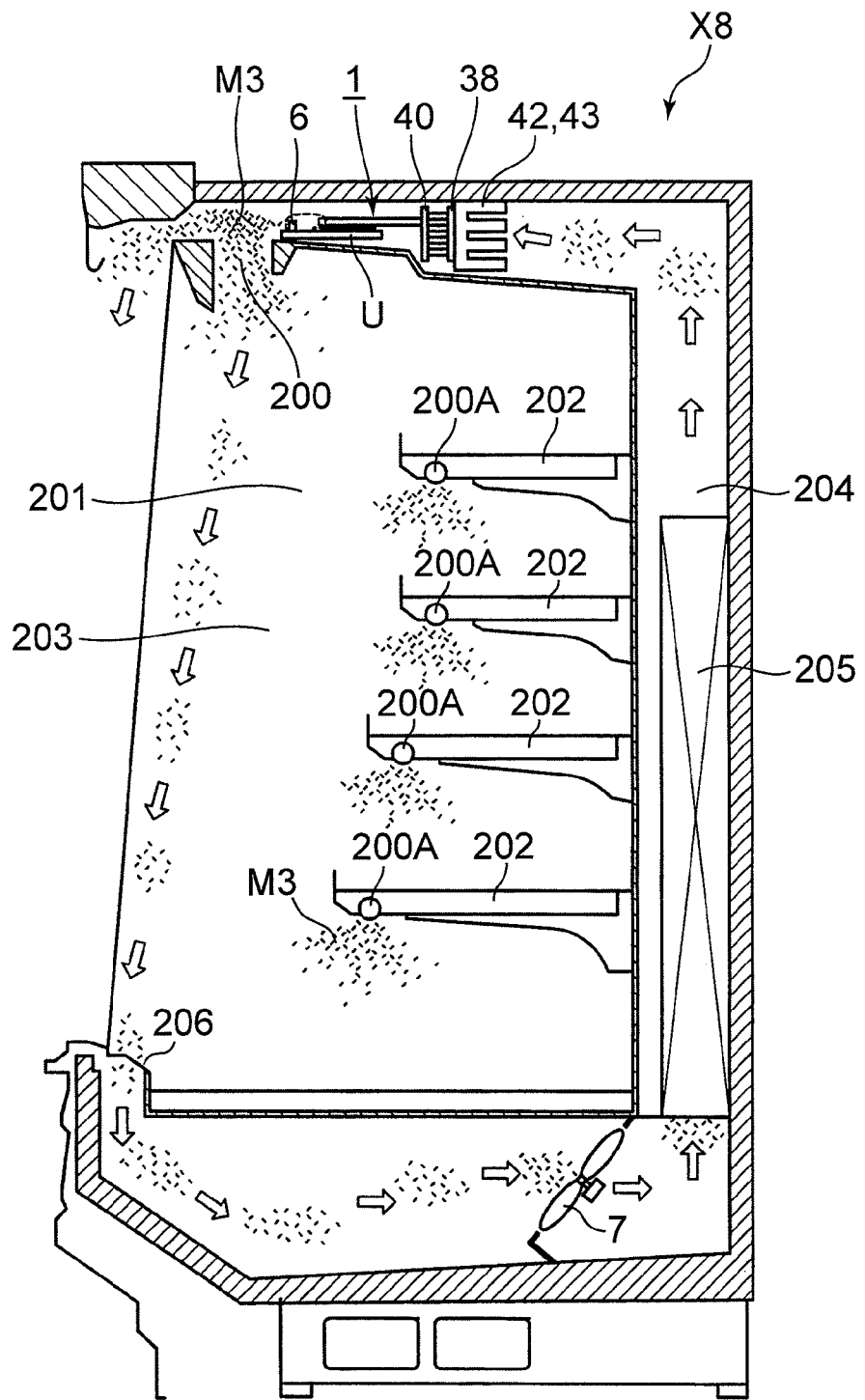
FIG. 20 shows the usage mode 5 of the reduced water mist generating device according to one embodiment of the present invention.

FIG. 20 illustrates the usage mode 5 of the reduced water mist generating device of one embodiment of the present invention. In this figure, the elements identical to those of the reduced water mist generating device 1 shown in FIG. 6 are assigned with reference numerals identical to those shown in FIG. 6. Explanation of these elements is herein omitted.

[Usage Mode 5]

The reduced water mist generating device 1 shown in FIG. 20 is provided in a storage apparatus (electric apparatus) X8 including a storage unit for storing the storage object (for example, fresh food or flowers).

FIG. 20 shows a showcase (open showcase in FIG. 20) 203 serving as a storage unit for storing the storage objects. The showcase 203 is provided with a storage space 201, and rack shelves 202 are provided in the storage space 201.

Further, a ventilation channel 204 that passes from bottom to top of the storage apparatus X8 is provided in the showcase 203. One end of the ventilation channel 204 located in the lower portion of the storage apparatus X8 serves as a suction port 206 opened in the direction of the storage space 201. The other end positioned in the upper portion of the storage apparatus X8 serves as a blow-out port 200 opened in the direction of the storage space 201.

In the ventilation channel 204, an air blowing fan configured as the spraying section 7, a cooler 205, and the reduced water mist generating device 1 are provided in the order of description along the ventilation direction. Further, the ventilation channel 204 is branched toward each rack shelf 202, and each distal end portion of the ventilation channel in the branching direction serves as a blow-out port 200A opened in the storage space 201.

In the storage apparatus X8, the air sucked in from the suction port 206 is cooled by the cooling section 205. Further, in the storage apparatus X8, the cooled air is blown as a cold air flow by the spraying section (air blowing fan) 7 from the blow-out ports 200 and 200A into the storage space 201, thereby cooling the storage objects accommodated in the storage space 201.

Figure 21A:
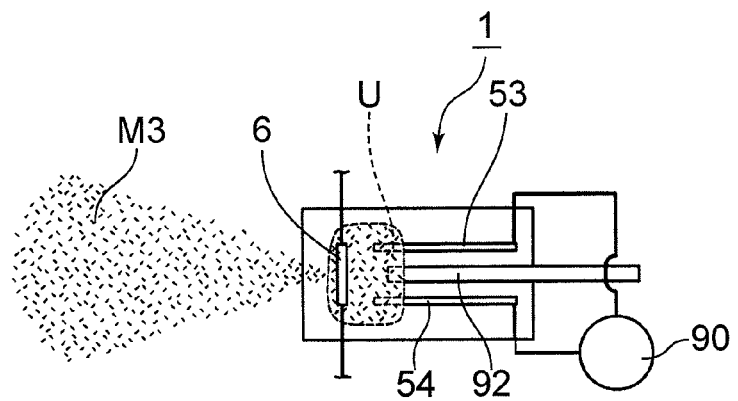
FIG. 21 show a configuration example of the reduced water mist generating device.
Figure 21B:
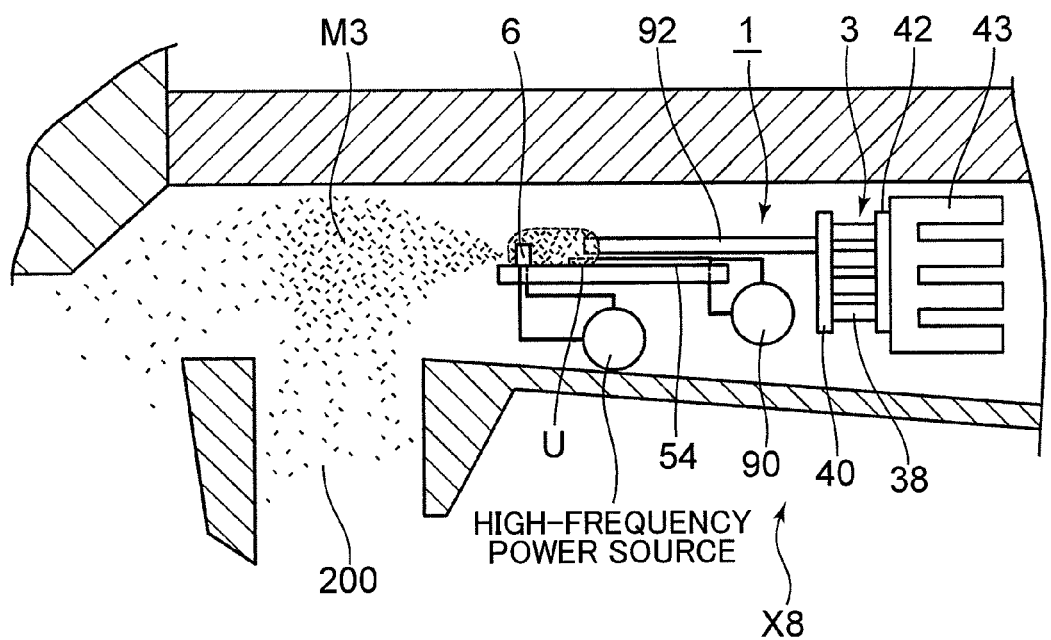

In the storage apparatus X8, the mist-like reduced water M3 is generated by the reduced water mist generating device 1 such as shown in FIGS. 21A, 21B, and the reduced water M3 is carried by the cooled air flow created by the spraying section (air flowing fan) 7 and released from the flow-out ports 200 and 200A into the storage space 201, thereby spraying the mist-like reduced water M3 onto the storage objects.

The reduced water mist generating device 1 shown in FIGS. 21A, 21B is used in the storage apparatus X8. The reduced water mist generating device 1 is configured identically to the reduced water mist generating device 1 shown in FIG. 6. Therefore, constituent elements thereof identical to those of the reduced water mist generating device 1 shown in FIG. 6 are assigned with same reference numerals and the explanation thereof is herein omitted.

In the reduced water mist generating device 1 shown in FIGS. 21A, 21B, the electrolysis section 90 is constituted by the anode 53 and cathode 54. In this electrolysis section 90, the reduced water M3 is generated at the cathode 54 side.

The reduced water M3 generally demonstrates an antioxidation effect and a reducing effect. In the storage apparatus X8 the storage objects are directly sprayed with the reduced water M3 as a reduced water mist. Therefore, deterioration of the storage objects caused by oxidation can be prevented and the degradation of color, taste, and nutritional value as well as browning and discoloration can be prevented. Further, since moisture can be supplied to the storage objects by spraying the reduced water M3, freshness of the storage objects can be preserved.

The showcase 203, a refrigeration truck X9, and a food storage unit X10 are described as storage units in the usage mode 5 and the below-described usage modes 6 and 7, but these examples are not limiting, and storage units at ships, airplanes, and freight trains can be also considered.

Figure 22:
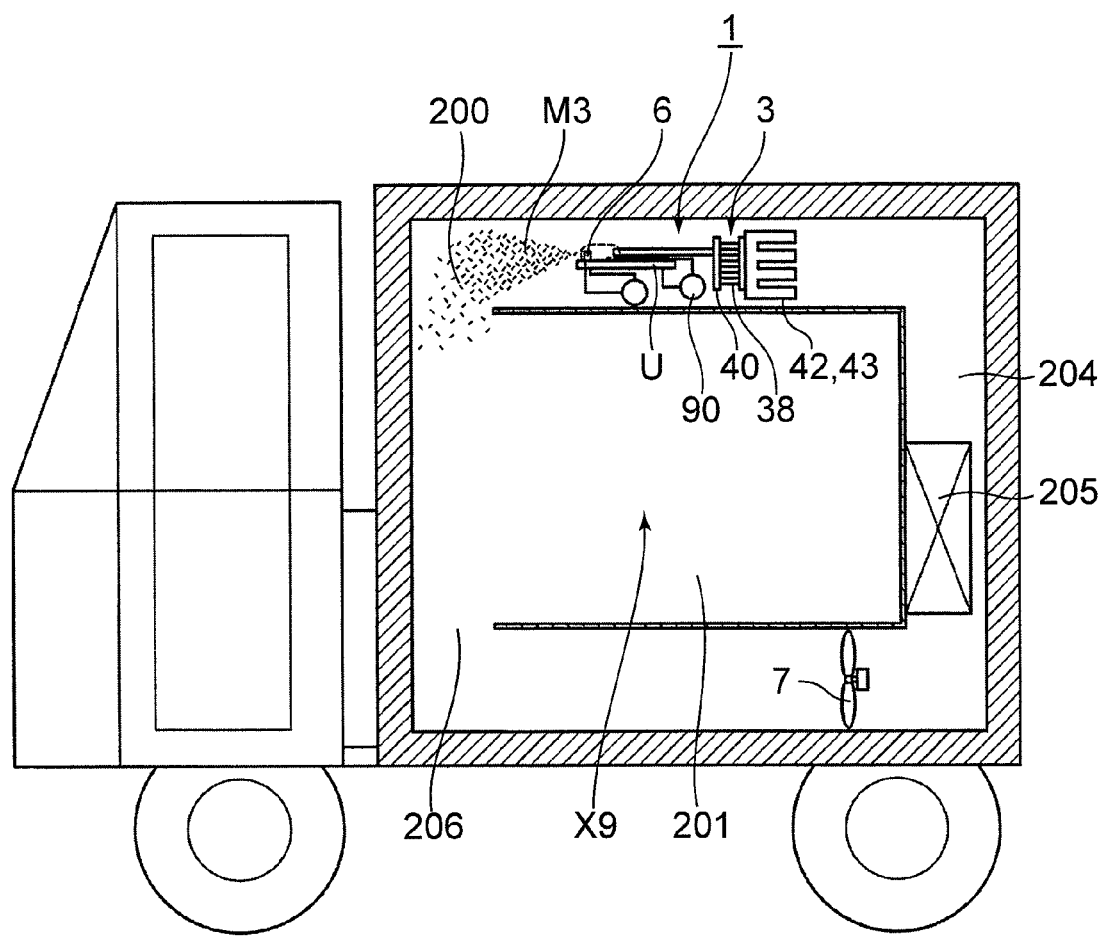
FIG. 22 shows the usage mode 6 of the reduced water mist generating device according to one embodiment of the present invention.
Figure 23:
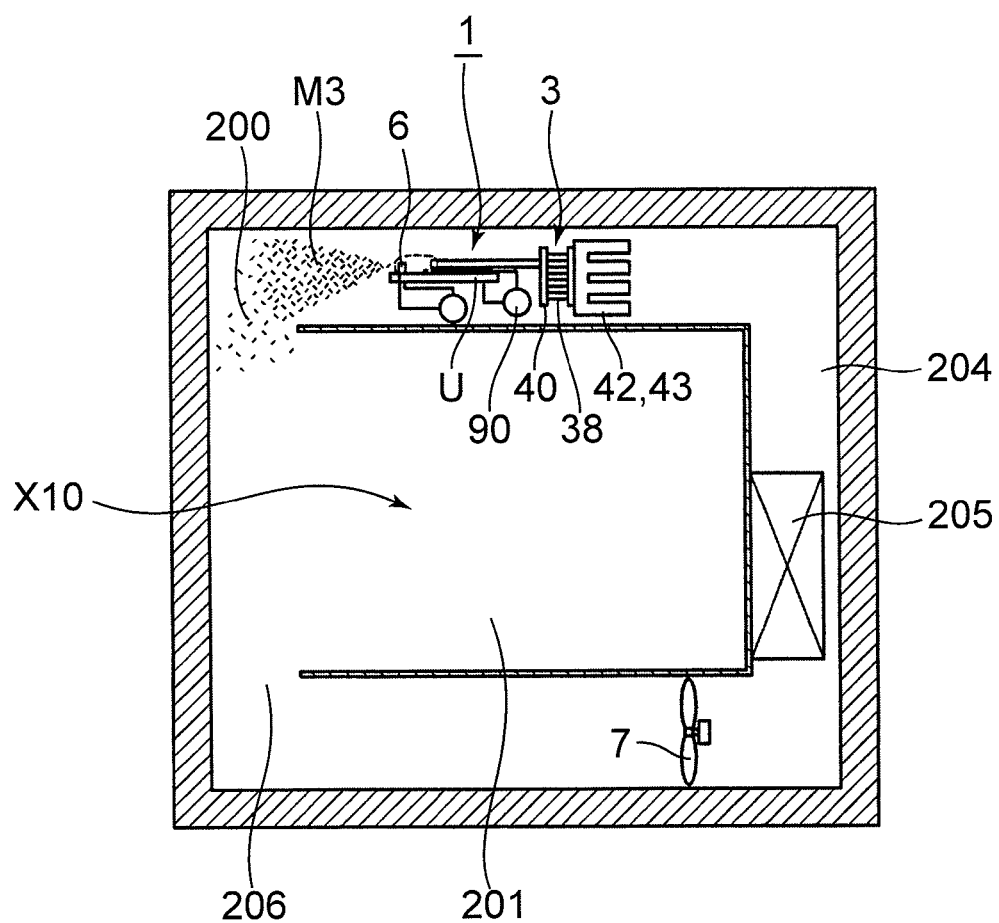
FIG. 23 shows the usage mode 7 of the reduced water mist generating device according to one embodiment of the present invention.

FIG. 22 and FIG. 23 respectively illustrate the usage modes 6 and 7 of the reduced water mist generating device of one embodiment of the present invention. The elements identical to those of the reduced water mist generating device 1 shown in FIG. 6 are assigned with reference numerals identical to those shown in FIG. 6. Explanation of these elements is herein omitted.

[Usage Modes 6 and 7]

The reduced water mist generating device 1 shown in FIG. 22 is provided in a refrigerated truck X9 that functions as a storage unit for storing the storage objects (for example, fresh food or flowers) (usage mode 6). The reduced water mist generating device 1 shown in FIG. 23 is provided in a food storage unit X10 that functions as a storage unit for storing the storage objects (for example, fresh food) (usage mode 7).

The reduced water mist generating device 1 shown in FIG. 22 and FIG. 23 uses the reduced water mist generating device 1 shown in FIGS. 21A, 21B in the same manner as in usage mode 5.

The refrigeration truck X9 and food storage unit X10 are each provided with a storage space 201. The refrigeration truck X9 and food storage unit X10 are also provided with a ventilation channel 204 passing from bottom to top. One end of the ventilation channel 204 that is positioned in the lower portion of the refrigeration truck X9 and food storage unit X10 has a suction port 206 opened in the direction of the storage space 201. The other end located in the upper portion of the refrigeration truck X9 and food storage unit X10 has a blow-out port 200 opened in the direction of the storage space 201.

In the ventilation channel 204, an air blowing fan constituted as the spraying section 7, a cooler 205, and the reduced water mist generating device 1 are provided in the order of description along the ventilation direction.

The mist-like reduced water M3 generated in the reduced water mist generating device 1 is fed by the air flow created by the spraying section (air blowing fan) 7 in the direction of the blow-out port 200. As a result, the reduced water M3 is sprayed as a reduced water mist onto the storage objects located in the storage space 201.

In the refrigeration truck X9 and food storage unit X10, the storage objects are directly sprayed with the reduced water M3 as a reduced water mist. Therefore, deterioration of the storage objects caused by oxidation can be prevented and the degradation of color, taste, and nutritional value as well as browning and discoloration can be prevented. Further, since moisture can be supplied to the storage objects by spraying the reduced water M3, freshness of the storage objects can be preserved.

Figure 24:
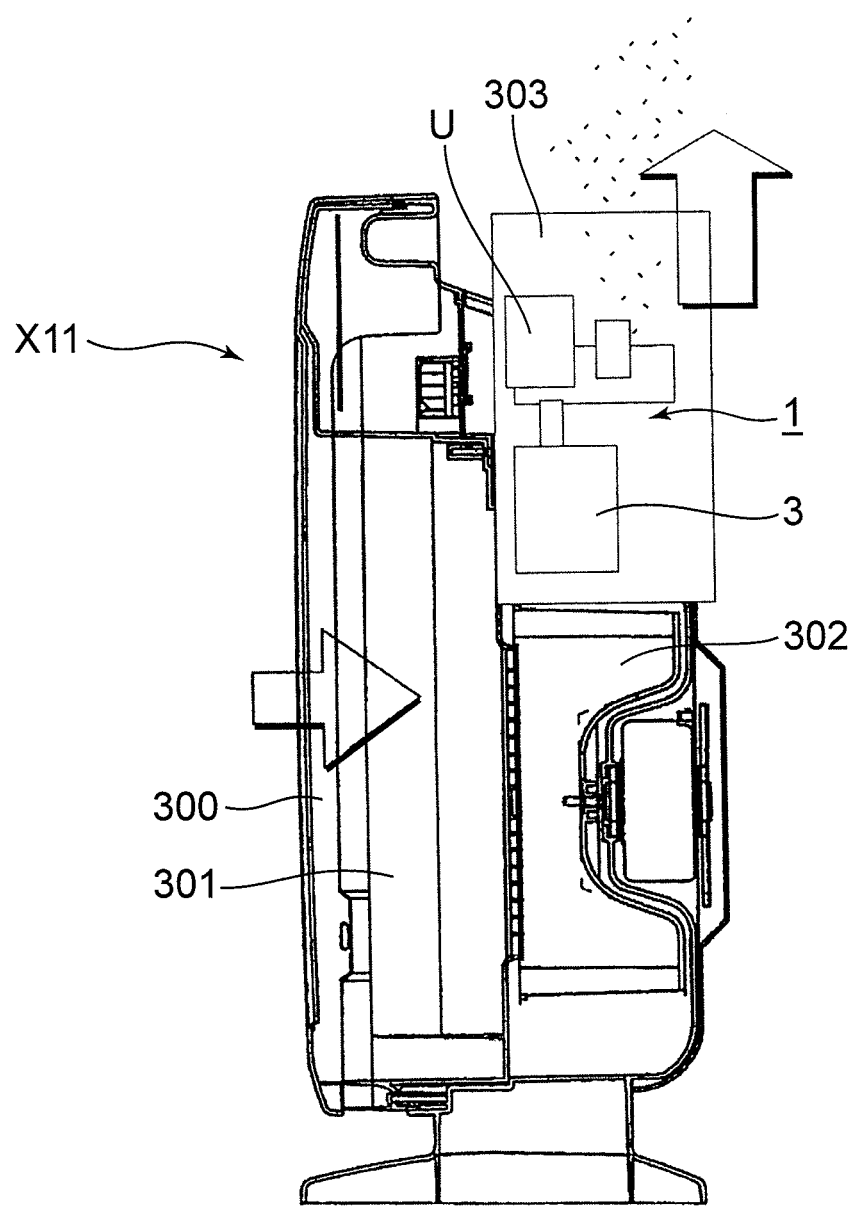
FIG. 24 shows the usage mode 8 of the reduced water mist generating device according to one embodiment of the present invention.

FIG. 24 illustrates the usage mode 8 of the reduced water mist generating device of one embodiment of the present invention. The elements identical to those of the reduced water mist generating device 1 shown in FIG. 2 are assigned with reference numerals identical to those shown in FIG. 2. Explanation of these elements is herein omitted.

[Usage Mode 8]

The reduced water mist generating device 1 shown in FIG. 24 is provided in an air purifier (electric apparatus) X11. The air purifier X11 includes a suction port 300, a filter 301, a fan 302, and a blow-out port 303. In the air purifier X11, the air sucked in from the suction port 300 is purified by the filter 301 and released to the outside from the blow-out port 303. In this case, the mist-like reduced water M3 generated by the reduced water mist generating device 1 is carried out by the pure air flow blown out from the blow-out port 303.

With such air purifier X11, the mist-like reduced water M3 from the reduced water mist generating device 1 is carried and released into the space by the pure air flow. Therefore, when the air purifier X11 is provided in a storage unit (for example, the showcase 203, refrigerated truck X9, and food storage unit X10), the reduced water M3 is uniformly sprayed as the reduced water mist onto the storage objects located in the storage unit.

When the air conditioner X4 (see FIG. 16) incorporating the reduced water mist generating device 1 is provided in the storage unit, the mist-like reduced water M3 carried by the air flow from the air conditioner X4 is also uniformly sprayed on all of the storage objects located in the storage unit.

Figure 25:
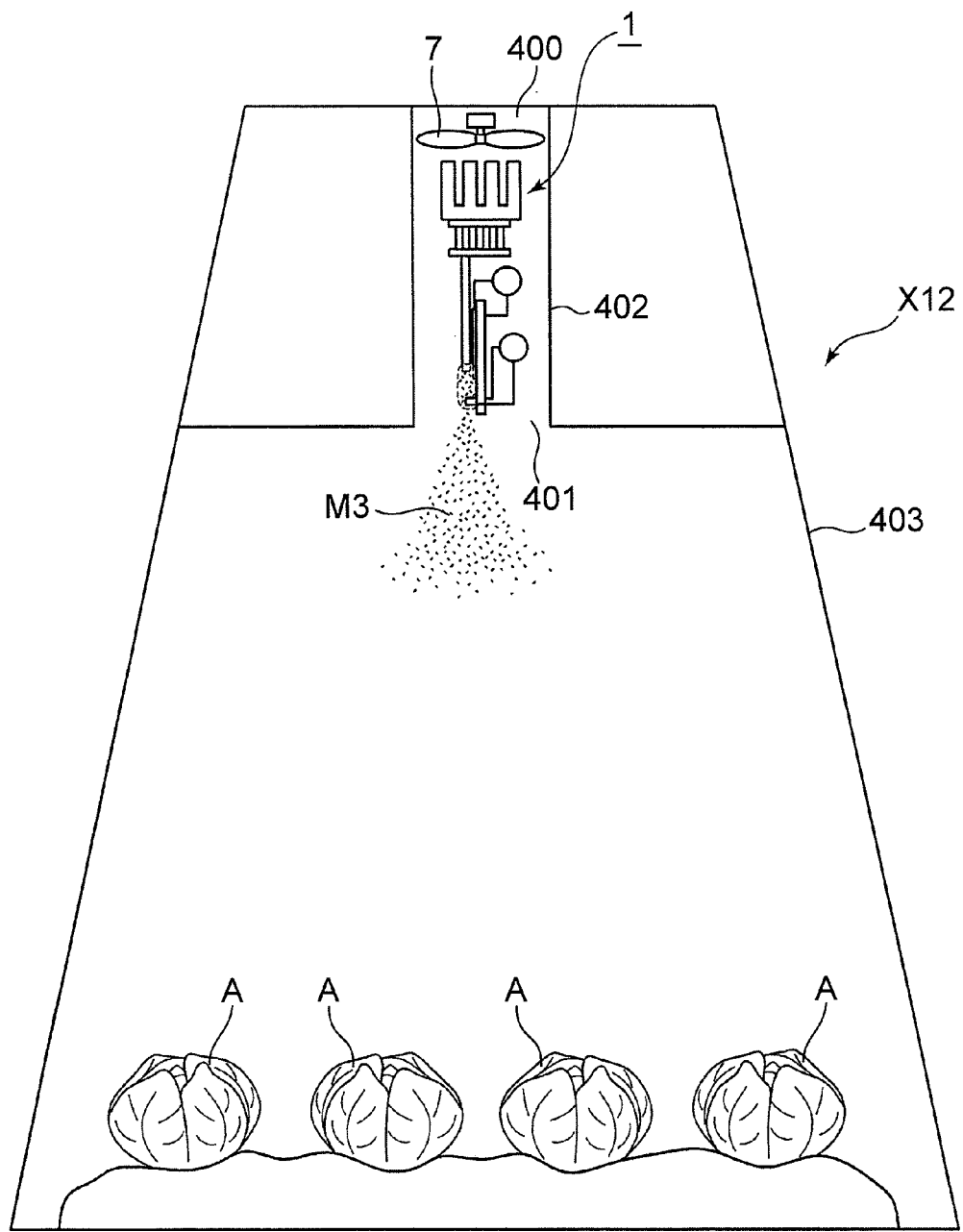
FIG. 25 shows the usage mode 9 of the reduced water mist generating device according to one embodiment of the present invention.

FIG. 25 illustrates the usage mode 9 of the reduced water mist generating device of one embodiment of the present invention. The elements identical to those of the reduced water mist generating device 1 shown in FIG. 6 are assigned with reference numerals identical to those shown in FIG. 6. Explanation of these elements is herein omitted.

[Usage Mode 9]

The reduced water mist generating device 1 shown in FIG. 25 is provided in a vinyl house X12 which is a plant growing site. The reduced water mist generating device 1 constitutes a plant growing device for growing plants A.

As shown in FIG. 25, a ventilation channel 402 having a suction port 400 and a blow-out port 401 is provided in the upper portion of the vinyl house X12. In the ventilation channel 402, an air blowing fan constituted as the spraying section 7 and the reduced water mist generating device 1 are provided in the order of description along the ventilation direction.

Further, in the ventilation channel 402, the suction port 400 is opened outside the vinyl house X12 or inside the vinyl house X12, and the blow-out port 401 is opened inside the vinyl house X12.

Figure 26:
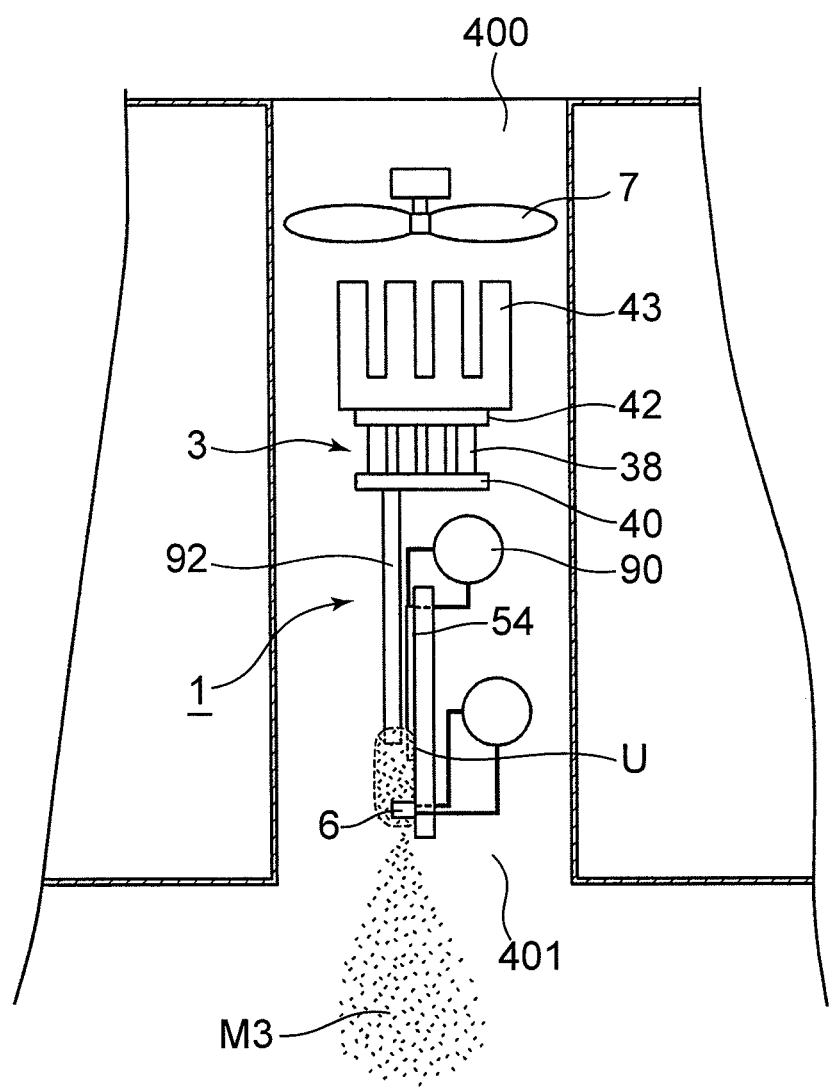
FIG. 26 shows a configuration example of the reduced water mist generating device.

In the vinyl house X12, the air sucked in through the suction port 400 is blown out from the blow-out port 401 via the ventilation channel 404 by the spraying section (air blowing fan) 7. In this case, the mist-like reduced water M3 generated by the reduced water mist generating device 1 such as shown in FIG. 26 is carried by the air flow passing through the ventilation channel 404. As a result, the mist-like reduced water M3 is carried and released inside the vinyl house X12 by the air flow passing through the ventilation channel 404. Therefore, the reduced water M3 is sprayed as a reduced water mist onto the plants A located inside the vinyl house X12.

In the vinyl house X12, the reduced water mist generating device 1 shown in FIG. 26 is used. This reduced water mist generating device 1 has the configuration identical to that of the reduced water mist generating device 1 shown in FIG. 6. Therefore, the elements identical to those of the reduced water mist generating device 1 shown in FIG. 6 are assigned with identical reference numerals and the explanation thereof is herein omitted.

In the reduced water mist generating device 1 shown in FIG. 26, the electrolysis section 90 is constituted by the anode 53 and cathode 54. In the electrolysis section 90, the reduced water M3 is generated at the cathode 54 side.

Thus, in the vinyl house X12, the reduced water M3 demonstrating an antioxidation effect and a reducing effect is sprayed as a reduced water mist onto growing plants A. As a result, deterioration of the plants A caused by oxidation can be prevented and degradation of color, taste, and nutritional value as well as browning and discoloration can be prevented. In addition, ozone damage of the plants A can be reduced. Further, since moisture can be supplied to the plants A by spraying the reduced water M3, the growth effect of plants A can be further improved.

When the reduced water atomizing section 6 that generates a reduced water mist by electrostatic atomization is provided, as shown in FIG. 9 and FIG. 10, in the reduced water mist generating device 1, a reduced water mist of a nanometer size containing radicals is sprayed on the plants A. As a result, the reduced water M3 penetrates into the structure of plants A and more significant antioxidation effect and reducing effect can be expected.

Where the air conditioner X4 shown in FIG. 16 or the air conditioner X11 shown in FIG. 24 is provided in the vinyl house X12, the mist-like reduced water M3 carried by the air flow from the air conditioner X4 or the air conditioner X11 is uniformly sprayed onto all of the plants A located in the vinyl house X12.

In the explanation above, the vinyl house X12 is shown as an example of a plant growing site, but this example is not limiting. For example, when plants are grown inside a building, the interior of the building is the plant growing site, and when plants are grown in an open field, the field is the plant growing site.

The above-described specific embodiments mainly include the invention having the below-described features.

The reduced water mist generating device according to one aspect of the present invention includes: a water acquiring section that acquires water for generating reduced water having dissolved therein a reduced component obtained by reducing cations generated by ionization of an acidic component in water; a reduced water generating unit that generates the reduced water from the water acquired by the water acquiring section; and a reduced water atomizing section that atomizes the reduced water generated by the reduced water generating unit to obtain mist-like reduced water.

With such a configuration, water acquired by the water acquiring section is converted by the reduced water generating unit into the reduced water, and the reduced water is atomized by the reduced water atomizing section to obtain mist-like reduced water. Since the mist-like reduced water is in a mist-like state, the reduced water drifts in the space and eventually arrives at the object.

Therefore, it is possible to generate and atomize the reduced water and provide the atomized reduced water as a reduced water mist. As a result, aging of the human skin can be inhibited, skin can be lubricated, and skin inflammation can be reduced. In addition, storage objects such as food can be stored for a long time.

In the above-described configuration, it is preferred that the water acquiring section include a heat radiating section in which a refrigerant gas is compressed to a high temperature and a high pressure and then caused to radiate heat to obtain a refrigerant liquid, and a cooling section in which the refrigerant liquid obtained in the heat radiating section is depressurized and then gasified to obtain the refrigerant gas, wherein moisture contained in air is caused to condensate by cooling with the cooling unit to acquire the water.

With such a configuration, water is acquired by condensation of moisture contained in the air by the cooling effect produced by the cooling section. Therefore, the user is not required to replenish water for generating the reduced water and the water can be acquired in a simple manner.

In the above-described configuration, it is preferred that the water acquiring section include a Peltier element that acquires the water by condensation of moisture contained in the air through cooling with a cooling surface.

With such a configuration, water is acquired by the Peltier element. Therefore, the user is not required to replenish water for generating the reduced water and the water can be acquired in a simple manner. Further, since the Peltier element has a small volume, the water acquiring section can be reduced in size. Furthermore, since the Peltier element generates no noise or vibrations, the water can be acquired without generating noise or vibrations.

In the above-described configuration, it is preferred that the water acquiring section include an adsorbent that adsorbs moisture contained in the air and a heater that heats the adsorber to desorb the moisture adsorbed by the adsorber.

With such a configuration, the operation of acquiring water for generating the reduced water and the operation of restoring the adsorption capacity of the adsorbent are repeatedly performed by repeatedly heating and not heating the adsorbent adsorbing moisture contained in the air with the heater. As a result, the user can acquire water in a simple manner, without replenishing water for generating the reduced water in the device.

Further, since the adsorbent adsorbs moisture contained in the art and the moisture adsorbed by the adsorbent is used to generate the reduced water, water for generating the reduced water can be acquired from the air, without energizing the device. Therefore, power consumption can be reduced.

In the above-described configuration, it is preferred that the reduced water generating unit include: an acidic aqueous solution generating section that generates an acidic component in water and generates an acidic aqueous solution containing cations and anions generated by ionization of the acidic component generated in the water; a reduced component generating section that generates a reduced component by providing electrons to the cations contained in the acidic aqueous solution and reducing the cations; and a reduced water generating section that dissolves the reduced component generated by the reduced component generating section in the water and generates reduced water in which the reduced component is dissolved, the acidic aqueous solution generating section includes: a storage section that stores water for generating the acidic aqueous solution or the acidic aqueous solution, and has a through hole formed in an outer wall thereof; a discharge section comprising a first electrode that is in contact with the water or the acidic aqueous solution stored in the storage section; an insulating spacer having a through hole communicating with the through hole of the outer wall; a second electrode that is provided to place the insulating spacer between the first electrode and the second electrode, and a high-voltage applying section for applying a high voltage to the first electrode and the second electrode, performing a creeping discharge in the through hole of the insulating spacer, and generating a source material for the acidic component; and an air blowing section that introduces an air flow into the through hole of the insulating spacer, generates the source material for the acidic component in the through hole in which the creeping discharge is being conducted, and dissolves the source material for the acidic component generated in the through hole in the water stored in the storage section to generate the acidic component.

With such a configuration, in the acidic aqueous solution generating section, the discharge section applies a high voltage to the first electrode and second electrode and induces a creeping discharge in the through hole of the insulating space. At the same time, the air blowing section introduces an air flow into the through hole and generates a large amount of bubbles that pass from the outside of the storage section via the through hole and into the water inside the storage section. As a result, a large amount of the starting material for an acidic component is generated in the through hole.

The starting material for an acidic component that has been generated in a large amount in the through hole is then introduced by the air flow created by the air blowing section into the storage section communicating with the through hole, thereby generating the acidic component at a high concentration in the water contained in the storage section. As a result, the acidic component present at a high concentration is ionized in the water contained in the storage section and the acidic aqueous solution containing at least cations (for example, hydrogen ions) at a high concentration is generated.

Further, with such a configuration, the reduced component generating section generates the reduced component by supplying electrons to the cations contained in the acidic aqueous solution and reducing the cations. Further, the reduced water generating section dissolves in water the reduced component generated by the reduced component generating section, thereby generating the reduced water having the reduced component dissolved therein.

Therefore, the reduced water is generated if the processing of generating the acidic aqueous solution, the processing of supplying electrons to the cations contained in the acidic aqueous solution generated by the aforementioned processing, reducing the cations, and generating the reduced component, and the processing of dissolving the reduced component generated by the aforementioned processing in water are performed successively. Therefore, the reduced water can be generated in a simple manner. Further, in the acidic aqueous solution generating section, the discharge section is disposed in a state in which the through hole of the insulating spacer communicates with the storage section. Therefore, the discharge section and storage section can be formed integrally in a compact manner and the entire device can be reduced in size.

In the above-described configuration, it is preferred that the water acquiring section acquire water for the acidic aqueous solution generating section to generate the acidic aqueous solution.

With such a configuration, since water for generating the acidic aqueous solution is acquired by the water acquiring section, the user is not required to replenish water for generating the acidic aqueous solution in the device.

In the above-described configuration, it is preferred that the outer wall be used as the insulating spacer, and the through hole of the outer wall be used as the through hole of the insulating spacer. Further, it is preferred that the outer wall is used as the first electrode.

With such configurations, the number of parts in the acidic aqueous solution generating section is reduced.

In the above-described configuration, it is preferred that the cations are hydrogen ions, and the reduced component generating section include: a reducing substance that is constituted by an element that is higher in ionization tendency than hydrogen and reduces the hydrogen ions contained in the acidic aqueous solution to generate hydrogen molecules as the reduced component, and an adjusting section that adjusts a generated amount of the hydrogen molecules.

With such a configuration, since the reduced component is constituted by an element that is higher in ionization tendency than hydrogen, the reducing substance generates hydrogen molecules as the reduced component by supplying electrons to the hydrogen ions contained in the acidic aqueous solution and becoming ions itself. Further, the generated amount of the hydrogen molecules is adjusted by the adjusting section.

Therefore, hydrogen molecules can be generated in a simple manner by using hydrogen ions contained in the acidic aqueous solution, while adjusting the generated amount of the hydrogen molecules. As a result, hydrogen molecules with a wide hydrogen concentration can be generated.

In the above-described configuration, it is preferred that the reducing substance could be attached to and detached from the adjusting section.

With such a configuration, since the reducing substance can be attached to and detached from the adjusting unit, when the reducing substance reduces hydrogen ions and the volume of the reducing substance decreases, the reducing substance that has decreased in volume can be removed from the adjusting section and a new reducing substance can be attached to the adjusting section.

In the above-described configuration, it is preferred that a range of immersion of the reducing substance into the acidic aqueous solution could be adjusted by the adjusting section.

With such a configuration, since a range of immersion of the reducing substance into the acidic aqueous solution can be adjusted by the adjusting unit, the generated amount of hydrogen molecules can be freely adjusted.

In the above-described configuration, it is preferred that the reduced water generating unit include an anode and a cathode for electrolyzing the water acquired by the water acquiring section, and generate hydrogen water as the reduced water at the cathode.

With such a configuration, the functions of the acidic aqueous solution generating section, reduced component generating section, and reduced water generating section are consolidated in the anode and cathode. Therefore, the structure of the reduced water generating unit is simplified and the unit can be miniaturized. Further, since hydrogen water is generated as the reduced water by electrolysis of water by the anode and cathode, the reducing substance for generating the reduced component becomes unnecessary, and the user is not required to replenish the reducing substance. Furthermore, since hydrogen water is generated as the reduced water by electrolysis of water by the anode and cathode, the user is not required to replenish the specimen serving as a basis for the reduced water.

In the above-described configuration, it is preferred that the reduced water generating unit have attached thereto an ascorbic acid cartridge loaded with ascorbic acid, and the reduced water pass through the ascorbic acid cartridge to obtain reduced water having ascorbic acid dissolved therein.

With such a configuration, the reduced water passes through the ascorbic acid cartridge, thereby forming the reduced water having ascorbic acid dissolved therein. As a result, the reduced water having ascorbic acid dissolved therein is sprayed.

Where such reduced water having ascorbic acid dissolved therein is sprayed on a human body, the immune strength is increased. Further, collagen is generated. Further, common cold is prevented or rapid recovery is ensured. Further, resistance to stress is increased. Further, generation of carcinogenic substances is inhibited.

In the above-described configuration, it is preferred that the reduced water atomizing section include an ultrasound emitting element that atomizes the reduced water by irradiation with ultrasound waves.

With such a configuration, since the reduced water is atomized by irradiation with ultrasound waves, a reduced water mist of a nanometer diameter can be sprayed.

In the above-described configuration, it is preferred that the reduced water atomizing section include a surface acoustic wave generating section that generates surface acoustic waves and atomizes the reduced water by the surface acoustic waves.

With such a configuration, since the reduced water is atomized by the surface acoustic waves from the surface acoustic wave generating unit, a large amount of reduced water mist can be generated.

It is preferred that the above-described configuration further include a substrate having a flat surface, wherein the surface acoustic wave generating section is provided on the surface, and a concave reduced water storage section that stores the reduced water is provided at a position on the surface, which faces the surface acoustic wave generating section.

With such a configuration, surface acoustic waves from the surface acoustic wave generating section propagates over the substrate surface and reach the surface of the reduced water stored in the concave reduced water storage section provided on the surface. As a result, the reduced water is atomized by the surface acoustic waves.

Since the reduced water is thus atomized as a result of the surface acoustic waves propagating over the substrate surface and reaching the reduced water surface, it is clear that the oscillation surface where the surface acoustic waves propagate is at the same level as the reduced water surface. Therefore, the configuration atomizing the reduced water can be reduced in size and the reduced water mist generating device can be made compact.

In the above-described configuration, it is preferred that the reduced water atomizing section include an electrostatic atomizing section that atomizes the reduced water by a high electric field generated by applying a high voltage.

With such a configuration, since the reduced water is atomized by electrostatic atomization, a large amount of a reduced water mist of a nanosize diameter can be sprayed.

In the above-described configuration, it is preferred that the reduced water atomizing section include a pressurizing section that pressurizes the reduced water and a plurality of small holes for ejecting the reduced water pressurized by the pressurizing section.

With such a configuration, since the reduced water pressurized by the pressurizing section is ejected from the plurality of small holes, the reduced water can be atomized in a large amount to obtain the mist-like reduced water.

In the above-described configuration, it is preferred that the reduced water atomizing section include a pressurizing section that pressurizes the reduced water and a small hole for ejecting the reduced water pressurized by the pressurizing section.

With such a configuration, since the reduced water pressurized by the pressurizing section is ejected from the small hole, the reduced water can be atomized in a large amount to obtain the mist-like reduced water.

The above-described configuration is preferably provided in an air conditioner that at least purifies air in a space and adjusts either of temperature and humidity.

With such a configuration, since the reduced water mist generating device is provided in an air conditioner, it is possible to provide an air conditioner performing a series of operations for generating reduced water from water, atomizing the generated reduced water, and spraying the atomized reduced water.

Further, the mist-like reduced water can be carried everywhere in the space on the flow of air blown out from the air conditioner. As a result, the reduced water can be sprayed on all of the objects such as skin, hair, and food, and efficient antioxidation effect and reducing effect can be produced on the objects.

The above-described configuration preferably further includes a spraying section that sprays, as a reduced water mist, the reduced water converted into the mist-like reduced water by the reduced water atomizing section, wherein the spraying section sprays the reduced water in the entire interior of a space.

With such a configuration, since the spraying section caused the reduced water to diffuse to the entire interior of the space, the reduced water can be sprayed everywhere in the space. As a result, the antioxidation effect and reducing effect can be produced on all of the objects within the space.

The above-described configuration preferably further includes a spraying section that sprays, as a reduced water mist, the reduced water converted into the mist-like reduced water by the reduced water atomizing section, wherein the spraying section sprays the reduced water directionally onto part of space interior.

With such a configuration, the reduced water is sprayed by the spraying section directionally onto part of space interior. As a result, the region in which the reduced water is sprayed is limited to part of the space interior and the reduced water is sprayed on the object with pinpoint accuracy. As a result, a large amount of the reduced water can be sprayed on the object.

In the above-described configuration, it is preferred that the air conditioner include a detection section that detects the presence of a human body, and the spraying section sprays the reduced water directionally toward the human body detected by the detection section.

With such a configuration, the presence of a human body is automatically detected by the detection section and the reduced water is sprayed in the respective direction. As a result, even if a human body moves, the reduced water is sprayed with pinpoint accuracy in the movement direction. Therefore, the antioxidation effect and reducing effect can be produced with good efficiency on the moving human body.

It is preferred that the above-described configuration be provided in a hairdressing-cosmetic device used for either or both of hairdressing and cosmetic applications, and a spraying section be further provided that sprays, as a reduced water mist, the reduced water converted into the mist-like reduced water by the reduced water atomizing section.

With such a configuration, since the reduced water mist generating device including the spraying section that sprays the mist-like reduced water as a reduced water mist is provided in a hairdressing-cosmetic device, the hairdressing-cosmetic device can perform a series of operations of generating the reduced water having the reduced component dissolved therein from water, atomizing the generated reduced water, and spraying the atomized reduced water.

Thus, the hairdressing-cosmetic device can directly spray the reduced water onto the human skin or hair. Therefore, the reduced water can be sprayed everywhere on the human skin or hair. As a result, the antioxidation effect and reducing effect can be produced on the human skin or hair. For example, the human hair can be provided with gloss and lubrication and hair growth and restoration can be enhanced. In addition, for example, aging of the human skin can be inhibited, skin can be lubricated, and skin inflammation can be reduced.

In the above-described configurations, the operations of acquiring the water, generating the reduced water, atomizing the reduced water, and spraying the reduced water can be performed at the following timings.

Thus, the operations of acquiring the water, generating the reduced water, atomizing the reduced water, and spraying the reduced water can be performed simultaneously. Alternatively, the acquisition of water and generation of the reduced water can be performed simultaneously and the atomization and spraying of the reduced water can be performed thereafter. Further, the acquisition of water can be performed and the generation of the reduced water, atomization of the reduced water, and spraying of the reduced water can be performed simultaneously thereafter.

It is preferred that the above-described configuration be provided in a hair care device for performing hair treatment and further include a spraying section that sprays, as a reduced water mist, the reduced water converted into the mist-like reduced water by the reduced water atomizing section, on the hair.

With such a configuration, the reduced water mist generating device that sprays mist-like reduced water as a reduced water mist onto hair is provided in a hair care device and the mist-like reduced water is sprayed on the hair. As a result, the hair care device performs a series of operations of generating the reduced water in which a reduced component is dissolved from water, atomizing the generated reduced water, and spraying the atomized reduced water can be performed.

Further, since the reduced water can be sprayed onto every portion of human hair or skin, the hair can be provided with gloss and lubrication, hair oxidation can be prevented, and hair growth and restoration can be enhanced. Further, the hair coated with a perm liquid or dyeing liquid and damaged due to oxidation by electrons can be reduced, thereby restoring the hair.

In the above-described configuration, the operations of acquiring the water, generating the reduced water, atomizing the reduced water, and spraying the reduced water can be performed at the following timings.

Thus, the operations of acquiring the water, generating the reduced water, atomizing the reduced water, and spraying the reduced water can be performed simultaneously. Alternatively, the acquisition of water and generation of the reduced water can be performed simultaneously and the atomization and spraying of the reduced water can be performed thereafter. Further, the acquisition of water can be performed and the generation of the reduced water, atomization of the reduced water, and spraying of the reduced water can be performed simultaneously thereafter.

In the above-described configuration, it is preferred that the hair care device be a hair drier that sucks in and heats external air and then introduces the heated air as an air flow, and the spraying section spray the reduced water in a direction parallel to the air flow.

With such a configuration, the mist-like reduced water is sprayed in the direction parallel to the air flow from the hair drier. Therefore, the reduced water mist can be sprayed in a large amount on the hair.

It is preferred that the above-described configuration be provided in a storage device provided with a storage unit where a storage object is stored.

With such a configuration, the reduced water mist generating device generates mist-like reduced water inside the storage unit where the storage object is stored. As a result, since the reduced water diffuses in the storage unit, strong antioxidation effect and reducing effect can be produced on the storage object inside the storage unit. As a result, deterioration of the storage object caused by oxidation can be prevented and degradation of color, taste, and nutritional value as well as browning and discoloration can be prevented.

In the above-described configuration, it is preferred that the storage object be either or both of fresh food and flowers.

Fresh food and flowers generally deteriorate upon oxidation, and moisture is required to maintain the freshness thereof.

With such a configuration, since the mist-like reduced water is provided to either or both of fresh food and flowers, the oxidation of either or both of fresh food and flowers can be prevented. Further, moisture is supplied for maintaining freshness of food and flowers.

The above-described configuration is preferably installed in a plant growing site where plants are grown.

With such a configuration, the reduced water mist generating device generates mist-like reduced water in the plant growing site where plants are grown. As a result, the reduced water diffuses into the plant growing site and therefore strong antioxidation effect, reducing effect, and ozone damage preventing effect are produced on the plants in the plant growing site. As a result, deterioration of the plants caused by oxidation can be prevented, the degradation of color, taste, and nutritional value as well as browning and discoloration can be prevented, and plants can be effectively grown.

An electric apparatus according to another aspect of the present invention includes a reduced water mist generating device which is provided with: water acquiring section that acquires water for generating reduced water having dissolved therein a reduced component obtained by reducing cations generated by ionization of an acidic component in water; a reduced water generating unit that generates the reduced water from the water acquired by the water acquiring section; and a reduced water atomizing section that atomizes the reduced water generated by the reduced water generating unit to obtain mist-like reduced water.

With such a configuration, water acquired by the water acquiring section is converted by the reduced water generating unit into the reduced water, and the reduced water is atomized by the reduced water atomizing section to obtain mist-like reduced water. Such mist-like reduced water is eventually sprayed onto the object by the spraying section such as an air blowing fan.

As a result, a series of operations of generating the reduced water having the reduced component dissolved therein from water, atomizing the generated reduced water, and spraying the atomized reduced water can be performed. Further, since the reduced water is atomized and sprayed as mist-like reduced water, the reduced water can be delivered everywhere onto human hair or skin or to the storage objects such as food. As a result, aging of the human skin can be inhibited, skin can be lubricated, and skin inflammation can be reduced. In addition, storage objects such as food can be stored for a long time.

What is claimed is:

1. A reduced water mist generating device comprising:
   a water acquiring section that acquires water for generating reduced water having dissolved therein a reduced component obtained by reducing cations generated by ionization of an acidic component in water;
   a reduced water generating unit that generates the reduced water from the water acquired by the water acquiring section; and
   a reduced water atomizing section that atomizes the reduced water generated by the reduced water generating unit to obtain mist-like reduced water wherein
   the reduced water generating unit includes:
      an acidic aqueous solution generating section that generates an acidic component in water and generates an acidic aqueous solution containing cations and anions generated by ionization of the acidic component generated in the water;
      a reduced component generating section that generates a reduced component by providing electrons to the cations contained in the acidic aqueous solution and reducing the cations; and
      a reduced water generating section that dissolves the reduced component generated by the reduced component generating section in the water and generates reduced water in which the reduced component is dissolved.

2. The reduced water mist generating device according to claim 1, wherein
   the water acquiring section includes a heat radiating section in which a refrigerant gas is compressed to a high temperature and a high pressure and then caused to radiate heat to obtain a refrigerant liquid, and a cooling section in which the refrigerant liquid obtained in the heat radiating section is depressurized and then gasified to obtain the refrigerant gas, wherein
   moisture contained in air is caused to condensate by cooling with the cooling unit to acquire the water.

3. The reduced water mist generating device according to claim 1, wherein the water acquiring section includes a Peltier element that acquires the water by condensation of moisture contained in air through cooling with a cooling surface.

4. The reduced water mist generating device according to claim 1, wherein the water acquiring section includes an adsorbent that adsorbs moisture contained in air and a heater that heats the adsorber to desorb the moisture adsorbed by the adsorber.

5. The reduced water mist generating device according to claim 1, wherein
   the acidic aqueous solution generating section includes:
      a storage section that stores water for generating the acidic aqueous solution or the acidic aqueous solution, and has a through hole formed in an outer wall thereof;
      a discharge section comprising a first electrode that is in contact with the water or the acidic aqueous solution stored in the storage section; an insulating spacer having a through hole communicating with the through hole of the outer wall; a second electrode that is provided to place the insulating spacer between the first electrode and the second electrode, and a high-voltage applying section for applying a high voltage to the first electrode and the second electrode, performing a creeping discharge in the through hole of the insulating spacer, and generating a source material for the acidic component; and
      an air blowing section that introduces an air flow into the through hole of the insulating spacer, generates the source material for the acidic component in the through hole in which the creeping discharge is being conducted, and dissolves the source material for the acidic component generated in the through hole in the water stored in the storage section to generate the acidic component.

6. The reduced water mist generating device according to claim 1, wherein
   the water acquiring section acquires water for the acidic aqueous solution generating section to generate the acidic aqueous solution.

7. The reduced water mist generating device according to claim 5, wherein
   the outer wall is used as the insulating spacer, and
   the through hole of the outer wall is used as the through hole of the insulating spacer.

8. The reduced water mist generating device according to claim 5, wherein
   the outer wall is used as the first electrode.

9. The reduced water mist generating device according to claim 5, wherein
   the cations are hydrogen ions, and
   the reduced component generating section includes:
      a reducing substance that is constituted by an element that is higher in ionization tendency than hydrogen, and reduces the hydrogen ions contained in the acidic aqueous solution to generate hydrogen molecules as the reduced component, and
      an adjusting section that adjusts a generated amount of the hydrogen molecules.

10. The reduced water mist generating device according to claim 9, wherein
    the reducing substance can be attached to and detached from the adjusting section.

11. The reduced water mist generating device according to claim 9, wherein
    a range of immersion of the reducing substance into the acidic aqueous solution can be adjusted by the adjusting section.

12. The reduced water mist generating device according to claim 1, wherein the reduced water generating unit includes an anode and a cathode for electrolyzing the water acquired by the water acquiring section, and generates hydrogen water as the reduced water at the cathode.

13. The reduced water mist generating device according to claim 1, wherein
the reduced water generating unit has attached thereto an ascorbic acid cartridge loaded with ascorbic acid, and the reduced water passes through the ascorbic acid cartridge to obtain reduced water having ascorbic acid dissolved therein.

14. The reduced water mist generating device according to claim 1, wherein
the reduced water atomizing section includes an ultrasound emitting element that atomizes the reduced water by irradiation with ultrasound waves.

15. The reduced water mist generating device according to claim 1, wherein
the reduced water atomizing section includes a surface acoustic wave generating section that generates surface acoustic waves and atomizes the reduced water by the surface acoustic waves.

16. The reduced water mist generating device according to claim 15, further comprising a substrate having a flat surface, wherein
the surface acoustic wave generating section is provided on the surface, and
a concave reduced water storage section that stores the reduced water is provided at a position on the surface, which faces the surface acoustic wave generating section.

17. The reduced water mist generating device according to claim 1, wherein
the reduced water atomizing section includes an electrostatic atomizing section that atomizes the reduced water by a high electric field generated by applying a high voltage.

18. The reduced water mist generating device according to claim 1, wherein
the reduced water atomizing section includes a pressurizing section that pressurizes the reduced water and a plurality of small holes for ejecting the reduced water pressurized by the pressurizing section.

19. The reduced water mist generating device according to claim 1, wherein
the reduced water atomizing section includes a pressurizing section that pressurizes the reduced water and a small hole for ejecting the reduced water pressurized by the pressurizing section.

20. The reduced water mist generating device according to claim 1, which is provided in an air conditioner that at least purifies air in a space and adjusts either of temperature and humidity.

21. The reduced water mist generating device according to claim 20, further comprising
a spraying section that sprays, as a reduced water mist, the reduced water converted into the mist-like reduced water by the reduced water atomizing section, wherein
the spraying section sprays the reduced water in the entire interior of a space.

22. The reduced water mist generating device according to claim 20, further comprising
a spraying section that sprays, as a reduced water mist, the reduced water converted into the mist-like reduced water by the reduced water atomizing section, wherein
the spraying section sprays the reduced water directionally onto part of space interior.

23. The reduced water mist generating device according to claim 22, wherein
the air conditioner includes a detection section that detects the presence of a human body, and
the spraying section sprays the reduced water directionally toward the human body detected by the detection section.

24. The reduced water mist generating device according to claim 1, which is provided in a hairdressing-cosmetic device used for either or both of hairdressing and cosmetic applications, and further comprises
a spraying section that sprays, as a reduced water mist, the reduced water converted into the mist-like reduced water by the reduced water atomizing section.

25. The reduced water mist generating device according to claim 1, which is provided in a hair care device for performing hair treatment, and further comprises
a spraying section that sprays, as a reduced water mist, the reduced water converted into the mist-like reduced water by the reduced water atomizing section, on the hair.

26. The reduced water mist generating device according to claim 25, wherein
the hair care device is a hair drier that sucks in and heats external air and then introduces the heated air as an air flow, and
the spraying section sprays the reduced water in a direction parallel to the air flow.

27. The reduced water mist generating device according to claim 1, which is provided in a storage device provided with a storage unit where a storage object is stored.

28. The reduced water mist generating device according to claim 27, wherein the storage object is either or both of fresh food and flowers.

29. The reduced water mist generating device according to claim 1, which is installed in a plant growing site where plants are grown.

30. An electric apparatus, comprising a reduced water mist generating device which is provided with:
a water acquiring section that acquires water for generating reduced water having dissolved therein a reduced component obtained by reducing cations generated by ionization of an acidic component in water;
a reduced water generating unit that generates the reduced water from the water acquired by the water acquiring section; and
a reduced water atomizing section that atomizes the reduced water generated by the reduced water generating unit to obtain mist-like reduced water wherein
the reduced water generating unit includes:
an acidic aqueous solution generating section that generates an acidic component in water and generates an acidic aqueous solution containing cations and anions generated by ionization of the acidic component generated in the water;
a reduced component generating section that generates a reduced component by providing electrons to the cations contained in the acidic aqueous solution and reducing the cations; and
a reduced water generating section that dissolves the reduced component generated by the reduced component generating section in the water and generates reduced water in which the reduced component is dissolved.

* * * * *